United States Patent
Stürzl et al.

(10) Patent No.: US 11,970,744 B2
(45) Date of Patent: *Apr. 30, 2024

(54) METHOD FOR DETECTING AN INCREASED RISK OR INCIDENCE OF COLORECTAL CANCER

(71) Applicant: Siemens Healthcare Diagnostics Inc., Tarrytown, NY (US)

(72) Inventors: Michael Stürzl, Erlangen (DE); Roland S. Croner, Erlangen (DE); Andreas Konrad, Erlangen (DE)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 348 days.

This patent is subject to a terminal disclaimer.

(21) Appl. No.: 17/304,068

(22) Filed: Jun. 14, 2021

(65) Prior Publication Data

US 2021/0317536 A1    Oct. 14, 2021

Related U.S. Application Data

(63) Continuation of application No. 16/275,596, filed on Feb. 14, 2019, now Pat. No. 11,066,710, which is a continuation of application No. 15/250,593, filed on Aug. 29, 2016, now Pat. No. 10,253,372, which is a continuation of application No. 14/433,080, filed as application No. PCT/US2013/062581 on Sep. 30, 2013, now abandoned.

(60) Provisional application No. 61/710,090, filed on Oct. 5, 2012.

(51) Int. Cl.
| | | |
|---|---|---|
| C12Q 1/68 | (2018.01) | |
| C12Q 1/6886 | (2018.01) | |
| G01N 33/574 | (2006.01) | |
| G16H 50/30 | (2018.01) | |

(52) U.S. Cl.
CPC ..... *C12Q 1/6886* (2013.01); *G01N 33/57419* (2013.01); *G16H 50/30* (2018.01); *C12Q 2600/112* (2013.01); *C12Q 2600/118* (2013.01); *C12Q 2600/158* (2013.01); *C12Q 2600/16* (2013.01); *G01N 2333/78* (2013.01); *G01N 2333/96494* (2013.01); *G01N 2800/50* (2013.01); *Y02A 90/10* (2018.01)

(58) Field of Classification Search
CPC ............ C12Q 1/6886; C12Q 2600/112; C12Q 2600/118; C12Q 2600/158; C12Q 2600/16; G01N 33/57419; G01N 2333/78; G01N 2333/96494; G01N 2800/50; G16H 50/30

See application file for complete search history.

(56) References Cited

U.S. PATENT DOCUMENTS

| | | | |
|---|---|---|---|
| 8,173,686 B2 | 5/2012 | Karlin et al. | |
| 10,253,372 B2 | 4/2019 | Sturzl et al. | |
| 11,066,710 B2* | 7/2021 | Stürzl | G16H 50/30 |
| 2008/0286799 A1 | 11/2008 | Waldman | |
| 2010/0009905 A1 | 1/2010 | Macina | |
| 2011/0123990 A1 | 5/2011 | Baker et al. | |
| 2013/0040852 A1* | 2/2013 | Anastassiou | C12Q 1/6886 |
| | | | 435/6.12 |
| 2014/0141986 A1* | 5/2014 | Spetzler | G01N 33/50 |
| | | | 435/7.1 |
| 2014/0206574 A1* | 7/2014 | Chapman | C12Q 1/6886 |
| | | | 506/16 |
| 2014/0323342 A1 | 10/2014 | Chapman | |

FOREIGN PATENT DOCUMENTS

| | | |
|---|---|---|
| WO | 2004074456 | 9/2004 |
| WO | 2011130435 | 10/2011 |
| WO | 2012167278 | 12/2012 |

OTHER PUBLICATIONS

International Search Report for PCT/US2013/062581 dated Jan. 7, 2014.
Anastassiou, D.; "A Mesenchymal Transition Signature Present in Invasive Solid Cancers;" MAGnet Newsletter. 5: 3-7, (2012).
Porte et al., "Neoplastic Progression of Human Colorectal Cancer is Associated With Overexpression of the Stromelysin-3 and BM-40/SPARC Genes", Int. J. Cancer, 64: 70-75, (1995).
Asano et al., "Prognostic Values of Matrix Metalloproteinase Family Expression in Human Colorectal Carcinoma", Journal of Surgical Research, 146: 32-42, (2008).
Skoglund et al., "Clinicopathological Significance of Stromelysin-3 Expression in Colorectal Cancer", Oncology, 67(1): 67-72, (2004).
Sanchez-Palencia et al., "Gene expression profiling reveals novel biomarkers in nonsmall cell lung cancer", International Journal of Cancer, vol. 129: 355-364, (2011).
Hung et al., "Multiple mRNA Markers for the Detection of Circulating Tumor Cells in Breast Cancer Patients", Genomic Medicine, Biomarkers, and Health Sciences, 4: 34-37, (2012).
Desmedt et al., "Characterization and Clinical Evaluation of CD10+ Stroma Cells in the Breast Cancer Microenvironment", Clinical Cancer Research, 18(4): 1004-1014, (2012).

* cited by examiner

Primary Examiner — Stephanie K Mummert

(57) ABSTRACT

The present invention relates to the methods and products for detection of colorectal cancer. Additionally, the present invention relates to methods and products for determining the probability, risk or incidence of colorectal cancer and of colorectal cancer metastasis. The products and methods of the present invention include detecting the level of expression of COL10A1 or MMP11, in combination, from samples, including tissue samples, from humans who currently have been diagnosed with cancer or who were previously diagnosed with cancer and those who are thought to have cancer and are undergoing diagnosis.

17 Claims, 18 Drawing Sheets

Specification includes a Sequence Listing.

800

METHOD FOR DETECTING AN INCREASED RISK OR INCIDENCE OF COLORECTAL CANCER

RELATED APPLICATIONS

The present application claims the benefit of U.S. patent application Ser. No. 15/250,593 filed Aug. 29, 2016, which claims the benefit of U.S. patent application Ser. No. 14/433,080 filed on Apr. 2, 2015, which is the US national stage of International Application No. PCT/US2013/062581 filed on Sep. 30, 2013, which claims priority to the U.S. provisional application No. 61/710,090, filed Oct. 5, 2012. All of the contents of these applications are incorporated herein by reference in their entirety.

This application incorporates by reference the sequence listing which is submitted together with this application in computer readable form which has the file name SL_2012P23093US03_ST25.txt and is 18 KB.

BACKGROUND

Colorectal cancer (CRC) is the third most common neoplasm worldwide. The mortality rate of newly diagnosed large bowel cancer approaches 50% and there has been little improvement over the past 40 years. Most of this mortality reflects local, regional and distant metastases.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. Similarly, diagnosis of metastatic or recurrent disease earlier potentially carries with it a better prognosis.

SUMMARY

COL10A1 and MMP11 expression in colorectal carcinoma primary tumors is associated with metastatic disease.

The present invention relates to the methods and products for detection of a disease, including cancer, including colon cancer, rectal cancer or colorectal cancer. Additionally, the present invention relates to methods and products for determining the probability, risk or incidence of a disease, such as cancer recurrence or metastasis in humans having cancer, including colon cancer, rectal cancer or colorectal cancer. Additionally, the present invention relates to methods and products for determining the probability, risk or incidence of metastasis in humans having cancer, including colon cancer, rectal cancer or colorectal cancer. The products and methods of the present invention include detecting the level of expression of COL10A1 or MMP11, individually or in combination, from samples, including tissue samples (e.g., from a primary tumor), from humans who currently have been diagnosed with cancer or who were previously diagnosed with cancer and those who are thought to have cancer and are undergoing diagnosis. The present invention additionally includes determining treatment options, including pharmaceutical and surgical treatment options, based on the probability, risk or incidence of disease recurrence, presence or metastasis, including instruction or administration of a particular drug based on the outcome.

In some embodiments, methods for identifying or characterizing individuals at risk of or suffering from colorectal cancer are provided that comprise providing a sample from an individual whose risk or incidence of colorectal cancer is to be identified or characterized, processing the sample to determine a level of COL10A1 and a level of MMP11, and classifying the individual as having an elevated risk or incidence of colorectal cancer if the levels of COL10A1 and MMP11 are both elevated relative to a reference. In some embodiments, the sample comprises human RNA. In some embodiments, the sample comprises human cDNA. In some embodiments, the step of processing comprises performing a PCR amplification of nucleic acids present in the sample. In certain embodiments, the step of processing comprises performing a reverse transcriptase PCR amplification of nucleic acids present in the sample. In some embodiments, the reverse transcriptase PCR amplification is quantitative. In certain embodiments, the step of processing comprises performing a microarray analysis of nucleic acids present in the sample. In some embodiments, the method further comprises administering to the individual a therapeutically effective amount of an agent for treating incidence and/or risk of colorectal cancer.

In some embodiments, methods of treating individuals at risk of or suffering from colorectal cancer are provided that comprise administering to the individual a therapeutically effective amount of an agent for treating incidence and/or risk of colorectal cancer, wherein a sample from the individual has previously been determined to contain an elevated level of both COL10A1 and MMP11 relative to a reference. In some embodiments, the sample comprises human RNA. In some embodiments, the sample comprises human cDNA.

In some embodiments, according to the methods presented herein, the individual comprises a human having colorectal cancer in stage UICC I. In some embodiments, the individual comprises a human having colorectal cancer in stage UICC II. In certain embodiments, the risk or incidence of colorectal cancer comprises a risk of progressing to stage UICC III and/or IV. In some embodiments, the risk or incidence of colorectal cancer comprises a risk or incidence of colorectal cancer metastasis. In certain embodiments, the risk or incidence of colorectal cancer comprises a risk or incidence of colorectal cancer recurrence.

In some embodiments, according to the methods presented herein, the sample comprises human tumor tissue. In some embodiments, the sample is obtained from a primary colorectal tumor.

In some embodiments, according to the methods presented herein, the reference comprises a historical reference level of COL10A1 and MMP11 from the individual whose risk or incidence of colorectal cancer is to be identified or characterized. In some embodiments, the reference comprises levels of COL10A1 and MMP11 in a sample from an individual with a known risk or incidence of colorectal cancer.

In some embodiments, kits for classifying individuals as having an elevated risk of or suffering from colorectal cancer are provided that comprise primers for amplifying a region of COL10A1 and primers for amplifying a region of MMP11. In some embodiments, the kit further comprises probes for detecting both COL10A1 and MMP11. In some embodiments, the kit further comprises amplification reagents. In some embodiments, amplification reagents are selected from the group consisting of polymerase, reverse transcriptase, nNTPs, $Mg^+$, and combinations thereof. In some embodiments, the kit further comprises a positive control. In certain embodiments, the kit further comprising a negative control. In some embodiments, the kit further comprises a positive and negative control.

In some embodiments, a non-transitory computer readable medium containing executable instructions that when executed cause a processor to perform operations is provided that comprises receiving an individual's levels of COL10A1 and MMP11, determining whether the individual possesses elevated levels of COL10A1 and MMP11 relative to a reference, and classifying the individual as at risk of or suffering from colorectal cancer if the individual possesses elevated levels of COL10A1 and MMP11. In some embodiments, the non-transitory computer readable medium further comprises executable instructions that when executed cause a processor to perform operations that comprise assigning a colorectal cancer classification identifier to the individual based on the levels of COL10A1 and MMP11, and outputting a list of colorectal cancer classifications of the individual. In some embodiments, the non-transitory computer readable medium further comprises instructions that when executed cause the processor to execute a step of ranking the colorectal cancer classifications before outputting the list of colorectal cancer classifications of the individual. In certain embodiments, the ranking is adjusted based on receiving a clinical response relating to the individual.

In some embodiments, a non-transitory computer readable medium containing executable instructions that when executed cause a processor to perform operations is provided that comprises receiving an individual's levels of COL10A1 and MMP11, determining whether the individual possesses elevated levels of COL10A1 and MMP11 relative to a reference, and classifying the individual as one that could benefit from therapy with an agent if the individual possesses elevated levels of COL10A1 and MMP11. In some embodiments, the non-transitory computer readable medium further comprises executable instructions that when executed cause a processor to perform operations that comprise assigning a treatment identifier to the individual based on the elevated levels of COL10A1 and MMP11, and outputting a list of agents suitable for administering to the individual. In some embodiments, the non-transitory computer readable medium further comprises instructions that when executed cause the processor to execute a step of ranking the agents before outputting the list of agents suitable for administering to the individual. In certain embodiments, the ranking is adjusted based on receiving a clinical response relating to the individual.

BRIEF DESCRIPTION OF THE DRAWING

FIGS. 5A and 5B show expression of collagen X and MMP11 at the protein level in colorectal carcinoma. Immunohistochemistry was performed on CRC specimen which exhibited in the prospective validation study either high or low RNA expression of the respective factors at the RNA level as indicated. Staining of the same specimen with the different antibodies were carried out on consecutive sections. High expression of collagen 10A1 was detected in panels B and H (arrows) and of MMP11 in panels D and K (arrows). Low expression was observed for collagen 10A1 in (A) and (G) and of MMP 11 in (E) and (J). Normal mucosa of the respective patients showed always lower signal intensities for both proteins (C, F). Control stainings of CRC tissues with an isotype antibody were negative (I, L).

DEFINITIONS

Figure 1A:
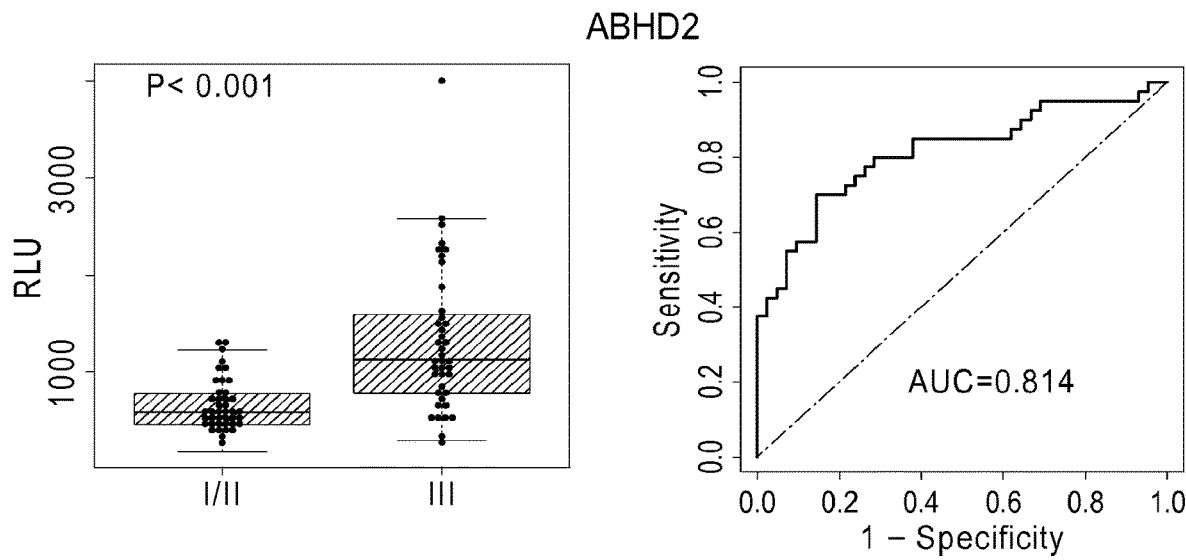
FIGS. 1A-1F Shows Molecular Markers of Metastatic CRC as Determined by microarray analysis. Box-plots (Figures A-E, left) and ROC analyses (Figures A-E, right) of gene expression of ABHD2 (A), COL10A1 (B), MMP11 (C), C8orf30A (D) and SLC35D1 (E) are shown. RNA was extracted from primary tumors in non-metastatic Union for International Cancer Control (UICC) stages I and II (n=40) and in metastatic stage UICC III (n=40). P values and areas under curve (AUC) are shown. Correlation analyses were carried out using scatterplot matrices and Spearman's rho values (F).
Figure 1B:
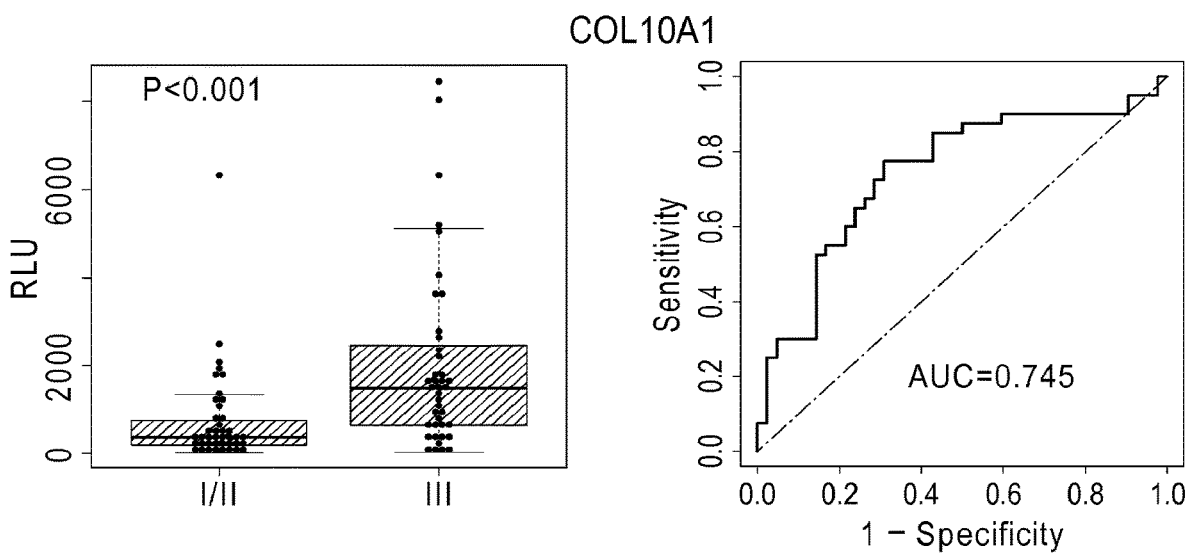
Figure 1C:
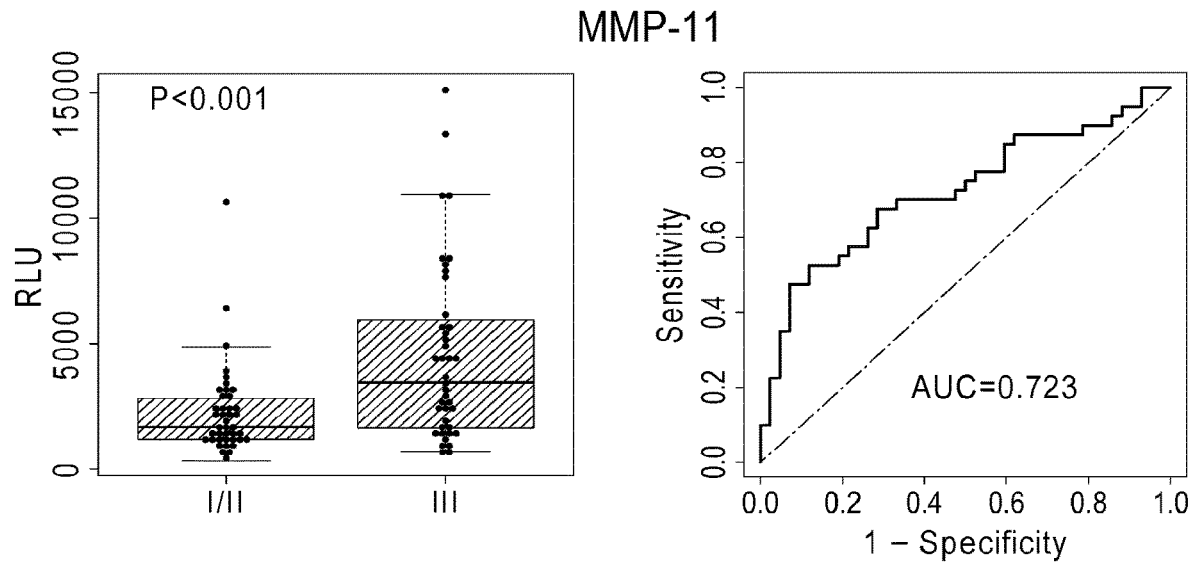
Figure 1D:
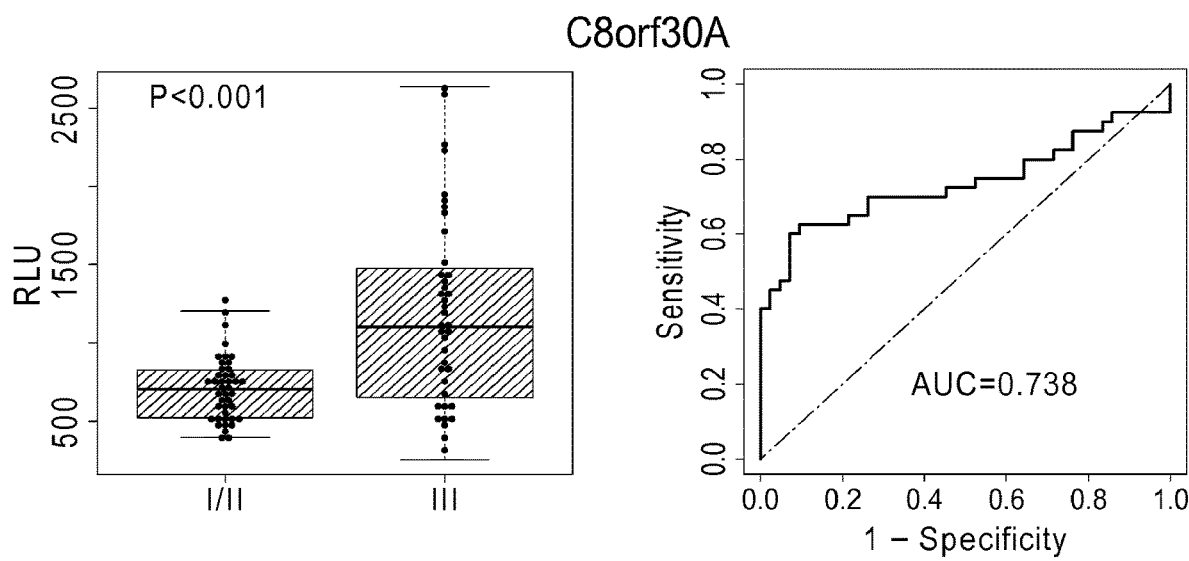
Figure 1E:
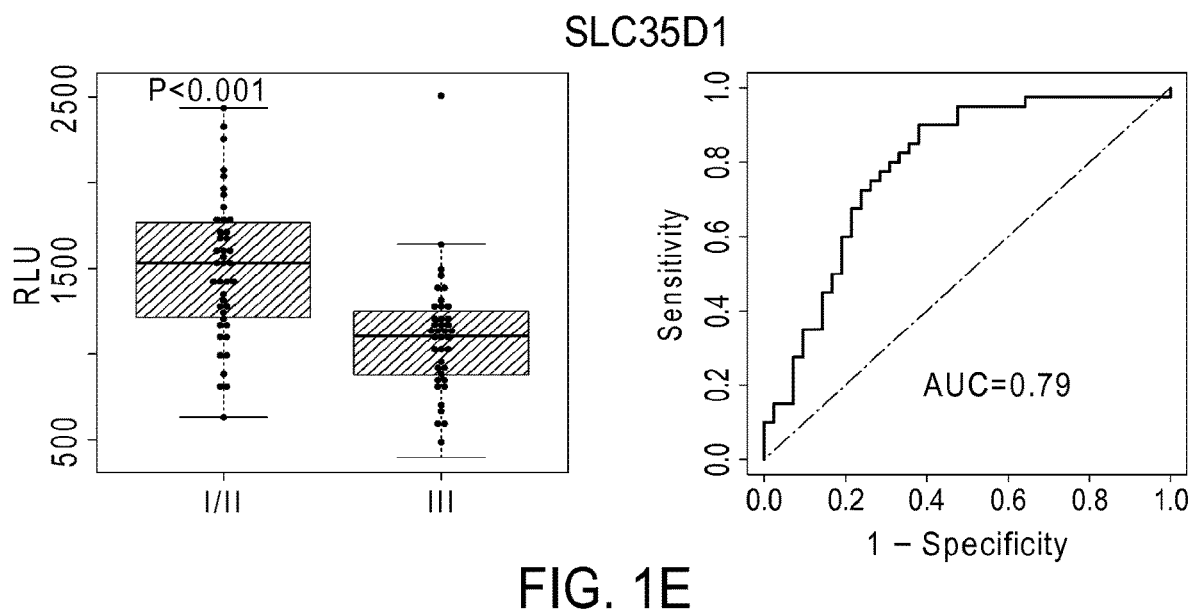

Agents: As used herein, the term "agents" refers to any compounds or compositions that act as modulators of colorectal cancer susceptibility or progression. In general, agents can be of any chemical class including, for example, polypeptides, nucleic acids, saccharides, lipids, small molecules, metals, or combinations thereof. In some embodiments, agents can be or comprise cells or organisms, or any fraction, extract, or component thereof. In some embodiments, agents are natural products in that they are found in and/or obtained from nature. In some embodiments, agents are man-made in that they are designed, engineered, and/or produced through action of the hand of man and/or are not found in nature. In some embodiments, agents are utilized in isolated or pure form; in some embodiments, agents are utilized in crude form. In some embodiments, potential agents are provided as collections or libraries, for example that may be screened to identify active agents within them. Some particular embodiments of agents that may be utilized in accordance with the present invention include small molecules, antibodies, antibody fragments, aptamers, siR-NAs, shRNAs, DNA/RNA hybrids, antisense oligonucleotides, ribozymes, peptides, peptide mimetics, polymers etc.

Antibody: As used herein, the term "antibody" refers to an immunoglobulin, or an antigen-binding fragment (e.g., Fab, Fab', F(ab')2, etc.) or derivative (e.g., s scFv, Fv, dsFv diabody, Fd). In some embodiments, an antibody is monoclonal. In some embodiments, an antibody is polyclonal. In some embodiments, an antibody is or comprises a polypeptide whose amino acid sequence includes all or a characteristic portion of an immunoglobulin constant domain (e.g., of an IgG, IgM, IgA, IgD, or IgE constant domain); in some such embodiments, the constant domain is a human constant domain. In some embodiments, an antibody is or comprises a polypeptide whose amino acid sequence includes all or a characteristic portion of an immunoglobulin variable domain; in some such embodiments the variable domain comprises CDR1, CDR2, and/or CDR3 sequence elements sufficient to permit and achieve specific binding to an antigen. In some such embodiments, one or more of such CDR1, CDR2, and CDR3 sequence elements is a human element. In some embodiments, an antibody is produced by synthesis. In some embodiments, an antibody is produced by a cell or cell line (e.g., a hybridoma). In some embodiments, an antibody is produced by an organism.

Associated With: The term "associated with" is used herein to describe an observed correlation between two items or events. For example, elevated expression of COL10A1 and MMP11 may be considered to be "associated with" colorectal cancer if its elevated expression correlates with a presence of colorectal cancer.

Carrier: As used herein, the term "carrier" refers to a pharmaceutically acceptable (e.g., safe and non-toxic for administration to a human) carrier substance useful for preparation of a pharmaceutical formulation. In many embodiments, a carrier is biologically substantially inert, e.g., so that activity of a biologically active substance is not materially altered in its presence as compared with in its absence. In some embodiments, a carrier is a diluent.

Comparable: The term "comparable" as used herein refers to a system, set of conditions, effects, or results that is/are sufficiently similar to a test system, set of conditions, effects, or results, to permit scientifically legitimate comparison. Those of ordinary skill in the art will appreciate and understand which systems, sets of conditions, effect, or results are sufficiently similar to be "comparable" to any particular test system, set of conditions, effects, or results as described herein.

Dosage form: As used herein, the terms "dosage form" and "unit dosage form" refer to a physically discrete unit of a therapeutic composition for administration to a subject to be treated. Each unit dosage form contains a predetermined quantity of active agent calculated to produce a desired therapeutic effect when administered in accordance with a dosing regimen. It will be understood, however, that a total dosage of the active agent may be decided by an attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses.

Gene: The term "gene", as used herein, has its art understood meaning, and refers to a part of the genome specifying a macromolecular product, be it DNA for incorporation into a host genome, a functional RNA molecule or a protein, and may include regulatory sequences (e.g., promoters, enhancers, etc.) and/or intron sequences preceding (5' non-coding sequences).

Nucleic Acid: The terms "nucleic acid", "nucleic acid molecule", and "polynucleotide" each is used herein to refer to a polymers of nucleotide monomers or analogs thereof, such as deoxyribonucleic acid (DNA) and ribonucleic acid (RNA). Unless otherwise stated, the terms encompass nucleic acid-like structures with synthetic backbones, as well as amplification products.

Polypeptide: The term "polypeptide" or "peptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" may be used to refer to the multiple polypeptides that are physically associated and function together as the discrete unit.

Primer: The terms "primer", as used herein, typically refers to oligonucleotides that hybridize in a sequence specific manner to a complementary nucleic acid molecule (e.g., a nucleic acid molecule comprising a target sequence). In some embodiments, a primer will comprise a region of nucleotide sequence that hybridizes to at least about 8, e.g., at least about 10, at least about 15, or about 20 to about 40 consecutive nucleotides of a target nucleic acid (i.e., will hybridize to a contiguous sequence of the target nucleic acid). In general, a primer sequence is identified as being either "complementary" (i.e., complementary to the coding or sense strand (+)), or "reverse complementary" (i.e., complementary to the anti-sense strand (−)). In some embodiments, the term "primer" may refer to an oligonucleotide that acts as a point of initiation of a template-directed synthesis using methods such as PCR (polymerase chain reaction) under appropriate conditions (e.g., in the presence of four different nucleotide triphosphates and a polymerization agent, such as DNA polymerase in an appropriate buffer solution containing any necessary reagents and at suitable temperature(s)). Such a template directed synthesis is also called "primer extension". For example, a primer pair may be designed to amplify a region of DNA using PCR. Such a pair will include a "forward primer" and a "reverse primer" that hybridize to complementary strands of a DNA molecule and that delimit a region to be synthesized and/or amplified.

Reference: As will be understood from context, a reference sequence, sample, population, agent or individual is one that is sufficiently similar to a particular sequence, sample, population, agent or individual of interest to permit a relevant comparison (i.e., to be comparable). In some embodiments, information about a reference sample is obtained simultaneously with information about a particular sample. In some embodiments, information about a reference sample is historical. In some embodiments, information about a reference sample is stored for example in a computer-readable medium. In some embodiments, comparison of a particular sample of interest with a reference sample establishes identity with, similarity to, or difference of a particular sample of interest relative to a reference. In some embodiments, a reference for a marker is based on levels measured in an individual or population of individuals (e.g., an average across the population of 5, 10, 20 or more individuals) who do not present with symptoms of the disease in question (e.g., colorectal cancer). In some embodiments, a reference for a marker comprises a historical reference level for the marker from the individual being characterized.

Risk: As will be understood from context, a "risk" of a disease, disorder or condition (e.g., colorectal cancer) comprises a likelihood that a particular individual will develop the disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition. In some embodiments a reference sample or group of reference samples are from individuals comparable to a particular individual. In some embodiments, relative risk is 0, 1, 2, 3, 4, 5, 6, 7, 8, 9, 10 or more.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids extracted from a sample or obtained by subjecting a primary sample to techniques such as amplification, isolation and/or purification of certain components, etc.

Suffering from: An individual who is "suffering from" a disease, disorder, and/or condition has been diagnosed with or displays one or more symptoms of the disease, disorder, and/or condition.

Therapeutically effective amount: As used herein, the term "therapeutically effective amount" refers to an amount of a therapeutic composition which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, a "therapeutically effective amount" refers to an amount of a therapeutic composition effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease. A therapeutically effective amount is commonly administered in a dosing regimen that may comprise multiple unit doses. A therapeutically effective amount (and/or an appropriate unit dose within an effective dosing regimen) may vary, for example, depending on route of administration, combination with other agents, etc.

Treatment: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

Colorectal Cancer

Colorectal cancer is the third most common neoplasm worldwide. The mortality rate of newly diagnosed large bowel cancer approaches 50% and there has been little improvement over the past 40 years. Most of this mortality reflects local, regional and distant metastases.

Colorectal cancer is a heterogeneous disease, consisting of tumors thought to emerge through three major molecular mechanisms: 1) mutations in the adenomatous polyposis coli (APC) gene, or the beta-catenin gene, combined with chromosomal instability, 2) mutations in DNA mismatch repair genes, such as MLH1, MSH2, PMS1, PMS2 and MSH6, associated with microsatellite instability and mutations in genes containing short repeats, and 3) gene silencing induced by hypermethylation of the promoter regions of tumor suppressor genes. The genetic complement of individual colorectal cancers is likely to include different combinations of genetic instability, specific mutations, and gene silencing. Chromosomal instability (CIN) is a common feature of cancers in general. It implies an aneuploid phenotype, in which whole chromosomes or large parts of them are being lost or gained.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. Similarly, diagnosis of metastatic or recurrent disease earlier potentially carries with it a better prognosis.

The invention presented herein comprises the recognition that the expression of certain genes, COL10A1 and MMP11 can serve as an indicator of increased risk or incidence of colorectal cancer.

COL10A1

Collagens are the major proteinaceous component of the extracellular matrix of mammalian species. The primary role of collagen is to provide a scaffold to support tissues, although a number of other functions have been elucidated for the collagens including roles in cell attachment, cell migration, filtration and morphogenesis. (Mays et al., Biochemical Journal, 1991, 276:307-313). Collagens are a super-family of closely related proteins sharing some common structural and functional properties, including triple-helical regions which have a repeating triplet of amino acids glycine-X-Y, where X is frequently proline and Y is often hydroxyproline. Hydroxyproline constitutes approximately 12% (w/w) of interstitial fibrillar collagens and is found in only a few other proteins including the complement component Cl q, elastin, acetylc holinesterase, conglutinin, type I and type II macrophage scavenger receptors, mannose-binding protein, pulmonary surfactant apolipoproteins A and D, where its prevalence is much lower than in collagens. (Mays and Laurent, in "Molecular Biology of Lung Disease" (Barnes and Stockley eds.) Blackwell Scientific Publishers, UK; 1994, pages 216-260.) Therefore, hydroxyproline is frequently used as an amino acid to identify and quantify collagens. (Udenfriend, Science, 1966, 152:1335-1340).

Currently, there are nineteen characterized collagens (designated collagens I to XIX). The gene COL10A1 encodes the protein collagen alpha-1(X) chain, the alpha chain of type X collagen. This type of collagen is typically expressed by hypertrophic chondrocytes during endochondral ossification.

Collagen, type X, alpha 1 protein contains 680 amino acid residues. Exemplary amino acid and nucleotide sequences from a full-length human collagen, type X, alpha 1 polypeptide are shown below as SEQ ID NOs: 1 and 2.

TABLE 1

| | |
|---|---|
| Human Collagen Alpha-1(X) Chain Precursor Protein Sequence (NCBI Reference Sequence: NP_000484.2) | MLPQIPFLLLVSLNLVHGVFYAERYQMPTGIKGPLPNTKTQFFIP YTIKSKGIAVRGEQGTPGPPGPAGPRGHPGPSGPPGKPGYGSPGL QGEPGLPGPPGPSAVGKPGVPGLPGKPGERGPYGPKGDVGPAGLP GPRGPPGPPGIPGPAGISVPGKPGQQGPTGAPGPRGFPGEKGAPG VPGMNGQKGEMGYGAPGRPGERGLPGPQGPTGPSGPPGVGKRGEN GVPGQPGIKGDRGFPGEMGPIGPPGPQGPPGERGPEGIGKPGAAG APGGQPGIPGTKGLPGAPGIAGPPGPPGFGKPGLPGLKGERGPAGL PGGPGAKGEQGPAGLPGKPGLTGPPGNMGPQGPKGIPGSHGLPGP KGETGPAGPAGYPGAKGERGSPGSDGKPGYPGKPGLDGPKGNPGL PGPKGDPGVGGPPGLPGPVGPAGAKGMPGHNGEAGPRGAPGIPGT RGPIGPPGIPGFPGSKGDPGSPGPPGPAGIATKGLNGPTGPPGPP GPRGHSGEPGLPGPPGPPGPPGQAVMPEGFIKAGQRPSLSGTPLV SANQGVTGMPVSAFTVILSKAYPAIGTPIPFDKILYNRQQHYDPR TGIFTCQIPGIYYFSYHVHVKGTHVWVGLYKNGTPVMYTYDEYTK GYLDQASGSAIIDLTENDQVWLQLPNAESNGLYSSEYVHSSFSGF LVAPM (SEQ ID NO: 1) |
| Human COL10A1 mRNA Sequence (NCBI Reference Sequence: NM_000493.3) | AAATGCTGAGCTAGGGGCAGGAGGCATGGGCGGGACAGTGTTCTG CACCTTCTGCACTGCTCATCTGGGCAGAGGAAGCTTCAGAAAGCT GCCAAGGCACCATCTCCAGGAACTCCCAGCACGCAGAATCCATCT GAGAATATGCTGCCACAAATACCCTTTTTGCTGCTAGTATCCTTG AACTTGGTTCATGGAGTGTTTTACGCTGAACGATACCAAATGCCC ACAGGCATAAAAGGCCCACTACCCAACACCAAGACACAGTTCTTC ATTCCCTACACCATAAAGAGTAAAGGTATAGCAGTAAGAGGAGAG CAAGGTACTCCTGGTCCACCAGGCCCTGCTGGACCTCGAGGGCAC CCAGGTCCTTCTGGACCACCAGGAAAACCAGGCTACGGAAGTCCT GGACTCCAAGGAGAGCCAGGGTTGCCAGGACCACCGGGACCATCA GCTGTAGGGAAACCAGGTGTGCCAGGACTCCCAGGAAAACCAGGA GAGAGAGGACCATATGGACCAAAAGGAGATGTTGGACCAGCTGGC CTACCAGGACCCCGGGGCCCACCAGGACCACCTGGAATCCCTGGA CCGGCTGGAATTTCTGTGCCAGGAAAACCTGGACAACAGGGACCC ACAGGAGCCCCAGGACCCAGGGGCTTTCCTGGAGAAAAGGGTGCA CCAGGAGTCCCTGGTATGAATGGACAGAAAGGGGAAATGGGATAT GGTGCTCCTGGTCGTCCAGGTGAGAGGGGTCTTCCAGGCCCTCAG GGTCCCACAGGACCATCTGGCCCTCCTGGAGTGGGAAAAAGAGGT GAAAATGGGGTTCCAGGACAGCCAGGCATCAAAGGTGATAGAGGT TTTCCGGGAGAAATGGGACCAATTGGCCCACCAGGTCCCCAAGGC CCTCCTGGGGAACGAGGGCCAGAAGGCATTGGAAAGCCAGGAGCT GCTGGAGCCCCAGGCCAGCCAGGGATTCCAGGAACAAAAGGTCTC CCTGGGGCTCCAGGAATAGCTGGGCCCCCAGGGCCTCCTGGCTTT GGGAAACCAGGCTTGCCAGGCCTGAAGGGAGAAAGAGGACCTGCT GGCCTTCCTGGGGGTCCAGGTGCCAAAGGGAACAAGGGCCAGCA GGTCTTCCTGGGAAGCCAGGTCTGACTGGACCCCCTGGGAATATG GGACCCCAAGGACCAAAAGGCATCCCGGGTAGCCCATGGTCTCCCA GGCCCTAAAGGTGAGACAGGGCCAGCTGGGCCTGCAGGATACCCT GGGGCTAAGGGTGAAAGGGGTTCCCCTGGGTCAGATGGAAAACCA GGGTACCCAGGAAAACCAGGTCTCGATGGTCCTAAGGGTAACCCA GGGTTACCAGGTCCAAAAGGTGATCCTGGAGTTGGAGGACCTCCT |

TABLE 1-continued

```
GGTCTCCCAGGCCCTGTGGGCCCAGCAGGAGCAAAGGGAATGCCC
GGACACAATGGAGAGGCTGGCCCAAGAGGTGCCCCTGGAATACCA
GGTACTAGAGGCCCTATTGGGCCACCAGGCATTCCAGGATTCCCT
GGGTCTAAAGGGGATCCAGGAAGTCCCGGTCCTCCTGGCCCAGCT
GGCATAGCAACTAAGGGCCTCAATGGACCCACCGGGCCACCAGGG
CCTCCAGGTCCAAGAGGCCACTCTGGAGAGCCTGGTCTTCCAGGG
CCCCCTGGGCCTCCAGGCCCACCAGGTCAAGCAGTCATGCCTGAG
GGTTTTATAAAGGCAGGCCAAAGGCCCAGTCTTTCTGGGACCCCT
CTTGTTAGTGCCAACCAGGGGGTAACAGGAATGCCTGTGTCTGCT
TTTACTGTTATTCTCTCCAAAGCTTACCCAGCAATAGGAACTCCC
ATACCATTTGATAAAATTTTGTATAACAGGCAACAGCATTATGAC
CCAAGGACTGGAATCTTTACTTGTCAGATACCAGGAATATACTAT
TTTTCATACCACGTGCATGTGAAAGGGACTCATGTTTGGGTAGGC
CTGTATAAGAATGGCACCCCTGTAATGTACACCTATGATGAATAC
ACCAAAGGCTACCTGGATCAGGCTTCAGGGAGTGCCATCATCGAT
CTCACAGAAAATGACCAGGTGTGGCTCCAGCTTCCCAATGCCGAG
TCAAATGGCCTATACTCCTCTGAGTATGTCCACTCCTCTTTCTCA
GGATTCCTAGTGGCTCCAATGTGAGTACACACAGAGCTAATCTAA
ATCTTGTGCTAGAAAAAGCATTCTCTAACTCTACCCCACCCTACA
AAATGCATATGGAGGTAGGCTGAAAAGAATGTAATTTTTATTTTC
TGAAATACAGATTTGAGCTATCAGACCAACAAACCTTCCCCCTGA
AAAGTGAGCAGCAACGTAAAAACGTATGTGAAGCCTCTCTTGAAT
TTCTAGTTAGCAATCTTAAGGCTCTTTAAGGTTTTCTCCAATATT
AAAAAATATCACCAAAGAAGTCCTGCTATGTTAAAAACAAACAAC
AAAAAACAAACAACAAAAAAAAATTAAAAAAAAAAACAGAAATA
GAGCTCTAAGTTATGTGAAATTTGATTTGAGAAACTCGGCATTTC
CTTTTTAAAAAGCCTGTTTCTAACTATGAATATGAGAACTTCTA
GGAAACATCCAGGAGGTATCATATAACTTTGTAGAACTTAAATAC
TTGAATATTCAAATTTAAAAGACACTGTATCCCCTAAAATATTTC
TGATGGTGCACTACTCTGAGGCCTGTATGGCCCCTTTCATCAATA
TCTATTCAAATATACAGGTGCATATATACTTGTTAAAGCTCTTAT
ATAAAAAAGCCCCAAAATATTGAAGTTCATCTGAAATGCAAGGTG
CTTTCATCAATGAACCTTTTCAAACTTTTCTATGATTGCAGAGAA
GCTTTTTATATACCCAGCATAACTTGGAAACAGGTATCTGACCTA
TTCTTATTTAGTTAACACAAGTGTGATTAATTTGATTTCTTTAAT
TCCTTATTGAATCTTATGTGATATGATTTTCTGGATTTACAGAAC
ATTAGCACATGTACCTTGTGCCTCCCATTCAAGTGAAGTTATAAT
TTACACTGAGGGTTTCAAAATTCGACTAGAAGTGGAGATATATTA
TTTATTTATGCACTGTACTGTATTTTTATATTGCTGTTTAAAACT
TTTAAGCTGTGCCTCACTTATTAAAGCACAAAATGTTTTACCTAC
TCCTTATTTACGACGCAATAAAATAACATCAATAGATTTTTAGGC
TGAATTAATTTGAAAGCAGCAATTTGCTGTTCTCAACCATTCTTT
CAAGGCTTTTCATTGTTCAAAGTTAATAAAAAAGTAGGACAATAA
AGTGAAAAAAAAAAAAAAAAA (SEQ ID NO: 2)
```

MMP11

Extracellular matrix (ECM) is a general term for the insoluble components which immobilize and adhere the various cells which make up multicellular organisms. Extracellular matrix is known to affect proliferation and differentiation of cells via cell adhesion, and includes principally collagen, fibronectin, laminin and the like. Extracellular matrix is known to be degraded by an extracellular matrix protease (matrix metalloproteinase or MMP, referred to below as "MMP"). MMP is an enzyme which is expressed in the course of tissue generation and differentiation via repeated cell division of a fertilized egg, and is also closely associated with invasion and metastasis of cancer. Degradation of extracellular matrix around cancer cells and in the vascular basal membrane is a necessary process for invasion and metastasis of cancer.

MMP11 encodes matrix metalloproteinase-11. In contrast to other MMPs, which are activated extracellularly, matrix metalloproteinase-11 is activated intracellularly by furin. MMP11 was originally identified through its overexpression in breast cancer and is thought to play an important role in cancer progression.

Metalloproteinase-11 protein contains 488 amino acid residues. Exemplary amino acid and nucleotide sequences from a full-length human metalloproteinase-11 polypeptide are shown below as SEQ ID NOs: 3 and 4.

TABLE 2

| Human Metallopeptidase 11 Prerotein Sequence (NCBI Reference Sequence: NP_001136401.1) | MAPAAWLRSAAARALLPPMLLLLLQPPPLLARALPPDAHHLHAER RGPQPWHAALPSSPAPAPATQEAPRPASSLRPPRCGVPDPSDGLS ARNRQKRFVLSGGRWEKTDLTYRILRFPWQLVQEQVRQTMAEALK VWSDVTPLTFTEVHEGRADIMIDFARYWHGDDLPFDGPGGILAHA FFPKTHREGDVHFDYDETWTIGDDQGTDLLQVAAHEFGHVLGLQH TTAAKALMSAFYTFRYPLSLSPDDCRGVQHLYGQPWPTVTSRTPA LGPQAGIDTNEIAPLEPDAPPDACEASFDAVSTIRGELFFFKAGF VWRLRGGQLQPGYPALASRHWQGLPSPVDAAFEDAQGHIWFFQGA QYWVYDGEKPVLGPAPLTELGLVRFPVHAALVWGPEKNKIYFFRG RDYWRFHPSTRRVDSPVPRRATDWRGVPSEIDAAFQDADGYAYFL RGRLYWKFDPVKVKALEGFPRLVGPDFFGCAEPANTFL (SEQ ID NO: 3) |

TABLE 2-continued

| | |
|---|---|
| Human MMP11 mRNA Sequence (NCBI Reference Sequence: NM_005940.3) | AAGCCCAGCAGCCCCGGGGCGGATGGCTCCGGCCGCCTGGCTCCG<br>CAGCGCGGCCGCGCGCGCCCTCCTGCCCCCGATGCTGCTGCTGCT<br>GCTCCAGCCGCCGCCGCTGCTGGCCCGGGCTCTGCCGCCGGACGC<br>CCACCACCTCCATGCCGAGAGGAGGGGGCCACAGCCCTGGCATGC<br>AGCCCTGCCCAGTAGCCCGGCACCTGCCCCTGCCACGCAGGAAGC<br>CCCCCGGCCTGCCAGCAGCCTCAGGCCTCCCCGCTGTGGCGTGCC<br>CGACCCATCTGATGGGCTGAGTGCCCGCAACCGACAGAAGAGGTT<br>CGTGCTTTCTGGCGGGCGCTGGGAGAAGACGGACCTCACCTACAG<br>GATCCTTCGGTTCCCATGGCAGTTGGTGCAGGAGCAGGTGCGGCA<br>GACGATGGCAGAGGCCCTAAAGGTATGGAGCGATGTGACGCCACT<br>CACCTTTACTGAGGTGCACGAGGGCCGTGCTGACATCATGATCGA<br>CTTCGCCAGGTACTGGCATGGGGACGACCTGCCGTTTGATGGGCC<br>TGGGGGCATCCTGGCCCATGCCTTCTTCCCCAAGACTCACCGAGA<br>AGGGGATGTCCACTTCGACTATGATGAGACCTGGACTATCGGGGA<br>TGACCAGGGCACAGACCTGCTGCAGGTGGCAGCCCATGAATTTGG<br>CCACGTGCTGGGGCTGCAGCACACAACAGCAGCCAAGGCCCTGAT<br>GTCCGCCTTCTACACCTTTCGCTACCCACTGAGTCTCAGCCCAGA<br>TGACTGCAGGGGCGTTCAACACCTATATGGCCAGCCCTGGCCCAC<br>TGTCACCTCCAGGACCCCAGCCCTGGGCCCCAGGCTGGGATAGA<br>CACCAATGAGATTGCACCGCTGGAGCCAGACGCCCCGCCAGATGC<br>CTGTGAGGCCTCCTTTGACGCGGTCTCCACCATCCGAGGCGAGCT<br>CTTTTTCTTCAAAGCGGGCTTTGTGTGGCGCCTCCGTGGGGGCCA<br>GCTGCAGCCCGGCTACCCAGCATTGGCCTCTCGCCACTGGCAGGG<br>ACTGCCCAGCCCTGTGGACGCTGCCTTCGAGGATGCCCAGGGCCA<br>CATTTGGTTCTTCCAAGGTGCTCAGTACTGGGTGTACGACGGTGA<br>AAAGCCAGTCCTGGGCCCCGCACCCCTCACCGAGCTGGGCCTGGT<br>GAGGTTCCCGGTCCATGCTGCCTTGGTCTGGGGTCCCGAGAAGAA<br>CAAGATCTACTTCTTCCGAGGCAGGGACTACTGGCGTTTCCACCC<br>CAGCACCCGGCGTGTAGACAGTCCCGTGCCCCGCAGGGCCACTGA<br>CTGGAGAGGGGTGCCCTCTGAGATCGACGCTGCCTTCCAGGATGC<br>TGATGGCTATGCCTACTTCCTGCGCGGCCGCCTCTACTGGAAGTT<br>TGACCCTGTGAAGGTGAAGGCTCTGGAAGGCTTCCCCCGTCTCGT<br>GGGTCCTGACTTCTTTGGCTGTGCCGAGCCTGCCAACACTTTCCT<br>CTGACCATGGCTTGGATGCCCTCAGGGGTGCTGACCCCTGCCAGG<br>CCACGAATATCAGGCTAGAGACCCATGGCCATCTTTGTGGCTGTG<br>GGCACCAGGCATGGGACTGAGCCCATGTCTCCTCAGGGGGATGGG<br>GTGGGGTACAACCACCATGACAACTGCCGGGAGGGCCACGCAGGT<br>CGTGGTCACCTGCCAGCGACTGTCTCAGACTGGGCAGGGAGGCTT<br>TGGCATGACTTAAGAGGAAGGGCAGTCTTGGGCCCGCTATGCAGG<br>TCCTGGCAAACCTGGCTGCCCTGTCTCCATCCCTGTCCCTCAGGG<br>TAGCACCATGGCAGGACTGGGGGAACTGGAGTGTCCTTGCTGTAT<br>CCCTGTTGTGAGGTTCCTTCCAGGGGCTGGCACTGAAGCAAGGGT<br>GCTGGGGCCCCATGGCCTTCAGCCCTGGCTGAGCAACTGGGCTGT<br>AGGGCAGGGCCACTTCCTGAGGTCAGGTCTTGGTAGGTGCCTGCA<br>TCTGTCTGCCTTCTGGCTGACAATCCTGGAAATCTGTTCTCCAGA<br>ATCCAGGCCAAAAAGTTCACAGTCAAATGGGGAGGGGTATTCTTC<br>ATGCAGGAGACCCCAGGCCCTGGAGGCTGCAACATACCTCAATCC<br>TGTCCCAGGCCGGATCCTCCTGAAGCCCTTTTCGCAGCACTGCTA<br>TCCTCCAAAGCCATTGTAAATGTGTGTACAGTGTGTATAAACCTT<br>CTTCTTCTTTTTTTTTTTTTAAACTGAGGATTGTCATTAAACACA<br>GTTGTTTTCTAAAAAAAAAAAAAAAA (SEQ ID NO: 4) |

Colorectal Cancer Diagnosis

The present invention encompasses the recognition that increased transcription of COL10A1 and MMP11 in combination is associated with a risk or incidence of colorectal cancer. In some embodiments, the present disclosure provides methods of classifying an individual at risk of or suffering from colorectal cancer. In general, such methods comprise obtaining a sample from the individual; processing the sample to determine levels of COL10A1 and MMP11; and classifying the individual as having an elevated risk or incidence of colorectal cancer if the levels of COL10A1 and MMP11 are both elevated relative to a reference.

In some embodiments, a risk of colorectal cancer comprises a risk from 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference. In some embodiments, a reference comprises an average occurrence of colorectal cancer in a population. In some embodiments, a reference comprises a statistical occurrence of colorectal cancer deemed to be acceptable or unavoidable in a population by medical professionals.

In some embodiments, an individual comprises a non-human animal. In some embodiments, a non-human animal comprises a mouse. In some embodiments, a non-human animal comprises a rat. In some embodiments, a non-human animal comprises a dog. In some embodiments, a non-human animal comprises a non-human primate. In some embodiments, an individual comprises a human. In some embodiments, an individual comprises a human having or suspected of having colorectal cancer. In some embodiments, an individual comprises a human having colorectal cancer in stage UICC I. In some embodiments, an individual comprises a human having colorectal cancer in stage UICC II.

In some embodiments, a sample is any sample comprising COL10A1 and MMP11. In some embodiments, a sample comprises cells from which COL10A1 and MMP11 is or can be obtained. In some embodiments, a sample comprises isolated nucleic acids. In some embodiments, a sample comprises human genomic DNA. In some embodiments the sample is or comprises cDNA. In some embodiments the sample is or comprises human RNA. In some embodiments the sample is or comprises human protein. In some embodiments, a sample is obtained (directly or indirectly) from a primary colorectal tumor.

In some embodiments, the individual is classified as having an elevated risk or incidence of colorectal cancer if the levels of COL10A1 and MMP11 are both elevated relative to a reference. In some embodiments, the individual is classified as having an elevated risk of metastasis if the levels of COL10A1 and MMP11 are both elevated relative to a reference.

In some embodiments, the individual is a human having colorectal cancer in stage UICC I and is classified as having an elevated risk of progressing to stage UICC III and/or IV if the levels of COL10A1 and MMP11 are both elevated relative to a reference. In some embodiments, the individual is a human having colorectal cancer in stage UICC II and is classified as having an elevated risk of progressing to stage UICC III and/or IV if the levels of COL10A1 and MMP11 are both elevated relative to a reference.

In some embodiments, the individual is classified as having an elevated risk of colorectal cancer recurrence if the levels of COL10A1 and MMP11 are both elevated relative to a reference. In some such embodiments, the individual is a human having colorectal cancer in stage UICC I or UICC II.

In some of these aforementioned embodiments, COL10A1 levels are increased 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference. In some embodiments, MMP11 levels are increased 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference.

In some embodiments, processing comprises processing a sample to detect levels of COL10A1 and MMP11 cDNA or RNA. As discussed in more detail below, in some embodiments primers are used in quantitative reverse transcriptase PCR and microarray methods for the amplification and detection of COL10A1 and MMP11 or fragments thereof. Methods of quantifying levels of mRNA transcripts are well known in the art and include but are not limited to northern analysis, semi-quantitative reverse transcriptase PCR, quantitative reverse transcriptase PCR, and microarray analysis. These and other basic RNA transcript detection procedures are described in Ausebel et al. (Ausubel F M, Brent R, Kingston R E, Moore D D, Seidman J G, Smith J A, Struhl K (eds). 1998. *Current Protocols in Molecular Biology*. Wiley: New York).

In some embodiments, the disclosed methods may involve some level of RNA preparation. Indeed, the template for an amplification reaction (e.g., a PCR reaction) is typically DNA and the target material to be analyzed is typically expressed RNA from human cells or tissue. As a result, the starting template material for the amplification reaction will often be cDNA which was generated from purified RNA. The RNA preparation step may be performed far removed from the actual amplification step, for example, in another laboratory, or at a much earlier time; however, in some embodiments the RNA isolation and preparation of the cDNA may occur in conjunction with the amplification step of the methods.

When an RNA preparation step is included in the disclosed methods, the method of RNA preparation can be any method of RNA preparation that produces enzymatically manipulatable mRNA. For example, the RNA can be isolated by using the guanidinium isothiocyanate-ultracentrifugation method, the guanidinium and phenol-chloroform method, the lithium chloride-SDS-urea method or poly A+/mRNA from tissue lysates using oligo(dT) cellulose method, e.g., see Chomczynski and Sacchi, *Anal. Biochem.* 162:156 (1987); and Auffray and Rougeon, *Eur. J. Biochem.* 107:303-314 (1980).

In some embodiments, disclosed methods involve cDNA preparation. The cDNA preparation step may be performed far removed from the actual amplification step, for example, in another laboratory, or at a much earlier time; however, in some embodiments the preparation of the cDNA may occur in conjunction with the amplification step of the methods.

When a cDNA preparation step is included in the disclosed methods, the method of cDNA preparation can be any method of cDNA preparation that produces enzymatically manipulatable cDNA. For example, the cDNA can be prepared by using, for example, random primers, poly-d(T) oligos, or NVd(T) oligos. For the purpose of data normalization, an equal amount of total RNA is typically used for cDNA synthesis. Many examples exist of performing reverse transcription to produce cDNA for use in PCR, including the following: Glisin et al., *Biochemistry* 13:2633-7 (1974); and Chirgwin et al., *Biochemistry* 18:5294-9 (1979).

Reverse transcriptases from any source (native or recombinant) may be used in the practice of the present disclosure. Suitable reverse transcriptases include, but are not limited to, those from Moloney murine leukemia virus (M-MLV), human T-cell leukemia virus type I (HTLV-I), bovine leukemia virus (BLV), Avian Sarcoma Leukemia Viruses (ASLV) including Rous Sarcoma Virus (RSV) and Avian Myeloblastosis Virus (AMV), human immunodeficiency virus (HIV), cauliflower mosaic virus, *Saccharomyces, Neurospora, Drosophila*, primates, and rodents.

The use of oligonucleotide sequences as primers to amplify COL10A1 and MMP11 in a sample is not limited to any particular nucleic acid amplification technique or any particular modification thereof. In fact, oligonucleotide sequences can be employed in any of a variety of nucleic acid amplification methods well-known in the art (see, for example, Kimmel and Berger, Methods Enzymol. 152: 307-316 (1987); Sambrook et al., "*Molecular Cloning: A Laboratory Manual*", 1989, $2^{nd}$ Ed., Cold Spring Harbour Laboratory Press: New York, NY; "*Short Protocols in Molecular Biology*", Ausubel (Ed.), 2002, $5^{th}$ Ed., John Wiley & Sons: Secaucus, NJ).

Nucleic acid amplification methods are well known in the art and include, but are not limited to, the Polymerase Chain Reaction (or PCR, described, for example, in U.S. Pat. Nos. 4,683,195, 4,683,202 and 4,889,818, each of which is incorporated herein by reference in its entirety). In its simplest form, PCR is an in vitro method for the enzymatic synthesis of specific DNA sequences, using two primers that hybridize to opposite strands and flank the region of interest in the target DNA. A plurality of reaction cycles, each cycle comprising: a denaturation step, an annealing step, and a polymerization step, results in the exponential accumulation of a specific DNA fragment. The termini of the amplified fragments are defined as the 5' ends of the primers. Examples of DNA polymerases capable of producing amplification products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq) which are available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs).

In some embodiments, the PCR reaction is a "kinetic PCR" (kPCR) or "kinetic RT-PCR" (kRT-PCR) reaction, which are also referred to as "real-time PCR" and "real-time RT-PCR," respectively. These methods involve detecting PCR products via a probe that provides a signal (typically a fluorescent signal) that is related to the amount of amplified product in the sample. Examples of commonly used probes used in kPCR and kRT-PCR include the following probes: TAQMAN® probes, Molecular Beacons probes, SCORPION® probes, and SYBR® Green probes. Briefly, TAQMAN® probes, Molecular Beacons, and SCORPION® probes each have a fluorescent reporter dye (also called a "fluor") attached on or around the 5' end of the probes and a quencher moiety attached on or around the 3' end of the probes. In the unhybridized state, the proximity of the fluor and the quench molecules prevents the detection of fluorescent signal from the probe. During PCR, when the polymerase replicates a template on which a probe is bound, the 5'-nuclease activity of the polymerase cleaves the probe at a site between the fluor and quencher thus, increasing fluorescence with each replication cycle. SYBR® Green probes bind double-stranded DNA and upon excitation emit light; thus as PCR product accumulates, fluorescence increases.

In some embodiments, the PCR reaction is used in a "single-plex" PCR assay. "Single-plex" refers to a single assay that is not carried out simultaneously with any other assays. Single-plex assays include individual assays that are carried out sequentially.

In some embodiments, the PCR reaction is used in a "multiplex" PCR assay. The term "multiplex" refers to multiple assays that are carried out simultaneously, in which detection and analysis steps are generally performed in parallel. Within the context of the present disclosure, a multiplex assay will include the use of the primers, alone or in combination with additional primers to identify, for example, COL10A1 and MMP11 simultaneously.

In some embodiments, the level of amplification product is assessed by microarray analysis.

In some embodiments, a first amplification step amplifies a region of a target gene. In some embodiments the amplification product is less than about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 250, 225, 200, 175, 150, 100, or 50 nucleotides long.

Colorectal Cancer Treatment

The present invention encompasses the recognition that individuals having an increased risk or incidence of colorectal cancer, as determined by elevated levels of COL10A1 and MMP11 in combination, can be treated with an agent for treating incidence and/or risk of colorectal cancer. In general, such methods comprise administering to the individual a therapeutically effective amount of an agent for treating incidence and/or risk of colorectal cancer, wherein a sample from the individual has previously been determined to contain an elevated level of both COL10A1 and MMP11 relative to a reference. In some embodiments, levels of COL10A1 and MMP11 are determined according to the methods described herein.

The present invention also encompasses the recognition that individuals having an increased risk of metastasis, as determined by elevated levels of COL10A1 and MMP11 in combination, may benefit from a different type of treatment than individuals with a reduced risk of metastasis. In particular, an individual with an increased risk of metastasis might receive a more aggressive type of treatment than an individual with a reduced risk of metastasis. Alternatively or additionally, an individual with an increased risk of metastasis might receive a treatment that is designed to reduce the likelihood of metastasis. In general, such methods comprise administering to the individual a therapeutically effective amount of an agent for treating incidence and/or risk of colorectal cancer and/or metastasis, wherein a sample from the individual has previously been determined to contain an elevated level of both COL10A1 and MMP11 relative to a reference. In some embodiments, levels of COL10A1 and MMP11 are determined according to the methods described herein.

In some embodiments, an agent for treating incidence and/or risk of colorectal cancer is or comprises RNA. In some embodiments, an agent is or comprises siRNA. In some embodiments, an agent is or comprises shRNA. In some embodiments, an agent is or comprises protein. In some embodiments, an agent is or comprises an antibody. In some embodiments, an agent is or comprises a chemical. In some embodiments, an agent is or comprises a chemotherapeutic agent. Examples of known chemotherapeutic agents include, but are not limited to, adriamycin, dexamethasone, vincristine, cyclophosphamide, fluorouracil, topotecan, taxol, interferons, platinum derivatives, taxane (e.g., paclitaxel), *vinca* alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others.

In accordance with the methods of the invention, an agent can be administered to a subject alone, or as a component of a composition or medicament (e.g., in the manufacture of a medicament for the prevention or treatment of colorectal cancer), as described herein. The compositions can be formulated with a physiologically acceptable carrier or excipient to prepare a pharmaceutical composition. The carrier and composition can be sterile. The formulation should suit the mode of administration. Methods of formulating compositions are known in the art (see, e.g., Remington's Pharmaceuticals Sciences, 17$^{th}$ Edition, Mack Publishing Co., (Alfonso R. Gennaro, editor) (2005)). Suitable pharmaceutically acceptable carriers are known in the art.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

An agent described herein (or a composition or medicament containing an agent described herein) is administered by any appropriate route. In some embodiments, an agent is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an agent is administered intravenously. In some embodiments, an agent is administered orally. In other embodiments, an agent is administered by direct administration to a target tissue, such as heart or muscle (e.g., intramuscular), tumor (intra-tumorallly), nervous system (e.g., direct injection into the brain; intraventricularly; intrathecally). Alternatively, an agent (or a composition or medicament containing an agent) can be administered by inhalation, parenterally, intradermally, transdermally, or transmucosally (e.g., orally or nasally). More than one route can be used concurrently, if desired.

In various embodiments, an agent is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating the underlying disease or condition). In some particular embodiments, appropriate doses or amounts to be administered may be extrapolated from dose-response curves derived from in vitro or animal model test systems.

In some embodiments, a composition is administered in a therapeutically effective amount and/or according to a dosing regimen that is correlated with a particular desired outcome (e.g., with treating or reducing risk for colorectal cancer).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, or combinations thereof).

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of colorectal cancer.

In some embodiments, a formulation comprising an agent described herein is administered as a single dose. In some embodiments, a formulation comprising an agent described herein is administered at regular intervals. Administration at an "interval," as used herein, indicates that the therapeutically effective amount is administered periodically (as distinguished from a one-time dose).

In some embodiments, a formulation comprising an agent described herein is administered at regular intervals indefinitely. In some embodiments, a formulation comprising an agent described herein is administered at regular intervals for a defined period.

Kits

In some embodiments, the present disclosure provides kits comprising materials useful for the amplification and detection of COL10A1 and MMP11. The inventive kits may be used by diagnostic laboratories, experimental laboratories, or practitioners.

Materials and reagents useful for the amplification and detection of COL10A1 and MMP11 according to the present disclosure may be assembled together in a kit. In some embodiments, an inventive kit comprises at least one primer set for each of COL10A1 and MMP11, and optionally, amplification reaction reagents. In some embodiments, the kit comprises nucleic acid detection probes.

Suitable amplification reaction reagents that can be included in an inventive kit include, for example, one or more of: buffers; enzymes having polymerase activity; enzyme cofactors such as magnesium or manganese; salts; nicotinamide adenide dinuclease (NAD); and deoxynucleoside triphosphates (dNTPs) such as, for example, deoxyadenosine triphospate; deoxyguanosine triphosphate, deoxycytidine triphosphate and deoxythymidine triphosphate, biotinylated dNTPs, suitable for carrying out the amplification reactions.

Depending on the procedure, the kit may further comprise one or more of: wash buffers and/or reagents, hybridization buffers and/or reagents, labeling buffers and/or reagents, and detection means. The buffers and/or reagents included in a kit are preferably optimized for the particular amplification/detection technique for which the kit is intended. Protocols for using these buffers and reagents for performing different steps of the procedure may also be included in the kit.

In some embodiments, the kit comprises a positive control. In some embodiments, a positive control comprises COL10A1 and/or MMP11 cDNA. In some embodiments, a kit comprises a negative control. In some embodiments, a negative control comprises any sequence not subject to amplification by primers useful for the amplification and detection of COL10A1 and MMP11. Furthermore, the kits may be provided with an internal control as a check on the amplification procedure and to prevent occurrence of false negative test results due to failures in the amplification procedure. An optimal internal control sequence is selected in such a way that it will not compete with the target nucleic acid sequence in the amplification reaction (as described above).

Kits may also contain reagents for the isolation of nucleic acids from biological specimen prior to amplification.

The reagents may be supplied in a solid (e.g., lyophilized) or liquid form. The kits of the present disclosure optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the amplification/detection assay may also be provided. The individual containers of the kit are preferably maintained in close confinement for commercial sale.

The kit may also comprise instructions for using the amplification reaction reagents, primer sets, and/or primer/probe sets according to the present disclosure. Instructions for using the kit according to one or more methods of the present disclosure may comprise instructions for processing the biological sample, extracting nucleic acid molecules, and/or performing the test; instructions for interpreting the results as well as a notice in the form prescribed by a governmental agency (e.g., FDA) regulating the manufacture, use or sale of pharmaceuticals or biological products.

Computer Systems

Methods described herein can be implemented in a computer system having a processor that executes specific instructions in a computer program. In some embodiments, the computer system may be arranged to output an individual's colorectal cancer classification based on receiving an individual's level of COL10A1 and MMP11. In some embodiments, a colorectal cancer classification comprises a colorectal cancer stage. In some embodiments, a colorectal cancer classification comprises metastatic or non-metastatic. In some embodiments, a colorectal cancer classification comprises a risk of developing colorecatal cancer. In some embodiments, the computer system may be arranged to output a medication profile based on receiving an individual's level of COL10A1 and MMP11. Particularly, the computer program may include instructions for the system to select the most appropriate medication (e.g., a chemotherapeutic drug) for an individual.

In some embodiments, the computer program may be configured such that the computer system can identify the individual's cancer classification based on received data and provide a preliminary identification of the universe of possible medications. The system may be able to rank-order the identified medications based on specific co-factors in the algorithmic equation. The system may be able to adjust the rank ordering based on the levels of COL10A1 and MMP11 in the individual. The system may be able to adjust the rank ordering based on clinical response relating to the individual (or of a family member of the individual who has or is suspected of having colorectal cancer).

Figure 6:
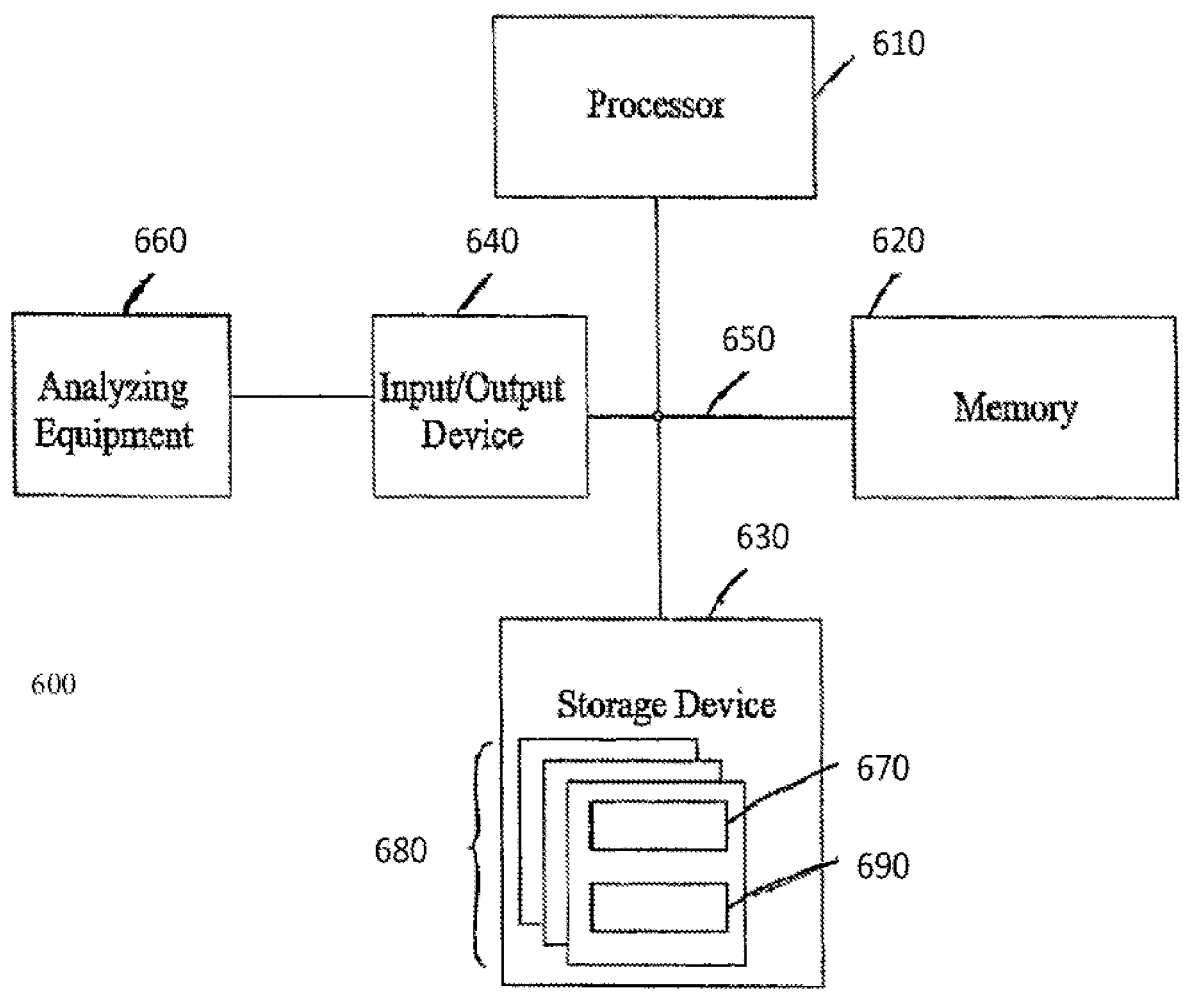
FIG. 6 depicts an exemplary block diagram of a computer system 100.

FIG. 6 is a block diagram of a computer system 600 that can be used in the operations described above, according to one embodiment. The system 600 includes a processor 610, a memory 620, a storage device 630 and an input/output device 640. Each of the components 610, 620, 630 and 640 are interconnected using a system bus 650. The system may include analyzing equipment 660 for determining the individual's levels of COL10A1 and MMP11.

The processor 610 is capable of processing instructions for execution within the system 600. In one embodiment, the processor 610 is a single-threaded processor. In another embodiment, the processor 610 is a multi-threaded processor. The processor 610 is capable of processing instructions stored in the memory 620 or on the storage device 630, including for receiving or sending information through the input/output device 640.

The memory 620 stores information within the system 600. In one embodiment, the memory 620 is a computer-readable medium. In one embodiment, the memory 620 is a volatile memory unit. In another embodiment, the memory 620 is a non-volatile memory unit.

The storage device 630 is capable of providing mass storage for the system 600. In one embodiment, the storage device 630 is a computer-readable medium. In various different embodiments, the storage device 630 may be a floppy disk device, a hard disk device, an optical disk device, or a tape device.

The input/output device 640 provides input/output operations for the system 600. In one embodiment, the input/output device 640 includes a keyboard and/or pointing device. In one embodiment, the input/output device 640 includes a display unit for displaying graphical user interfaces.

Figure 7:
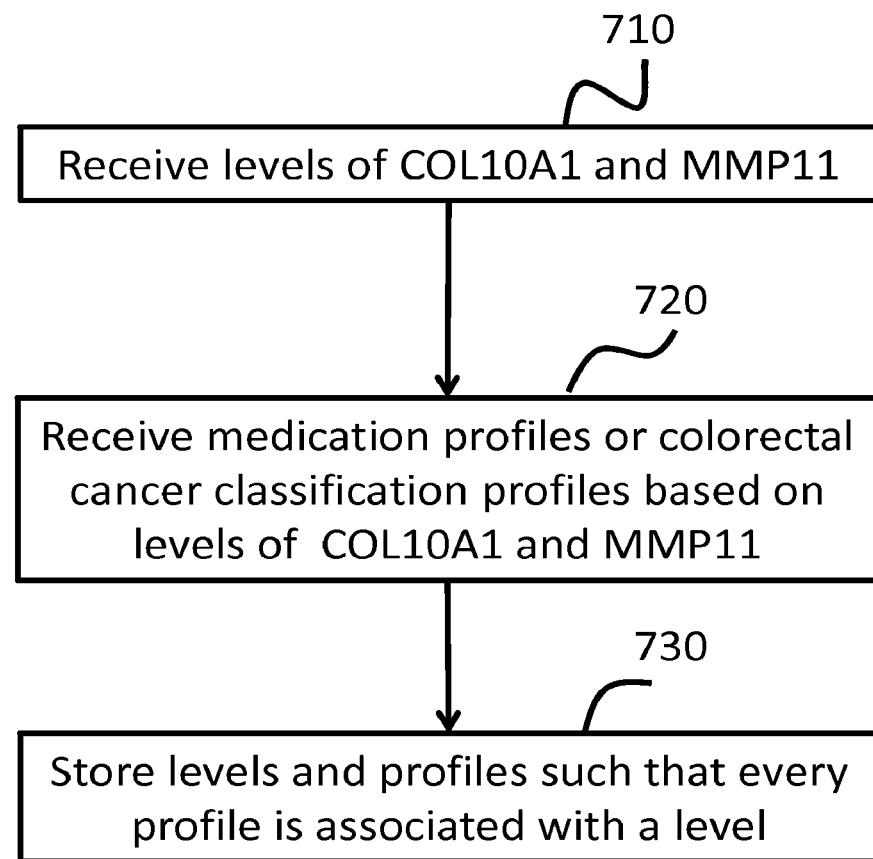
FIG. 7 depicts an exemplary flow chart of a method 200 for building a database for use in selecting a medication and/or colorectal cancer classification for a patient.

The system 600 can be used to build a database. FIG. 7 shows a flow chart of a method 700 for building a database for use in determining a colorectal cancer classification and/or selecting a medication for an individual. Preferably, the method 700 is performed in the system 600. For example, a computer program product can include instructions that cause the processor 610 to perform the steps of the method 700. The method 700 includes the following steps.

Receiving, in step 710, an individual's levels of COL10A1 and MMP11. A computer program in the system 600 may include instructions for presenting a suitable graphical user interface on input/output device 640, and the graphical user interface may prompt the user to enter the levels 670 using the input/output device 640, such as a keyboard.

Receiving, in step 720, a plurality of medication profiles or colorectal cancer classification profiles 680. The profiles 680 are specified based on the levels 670. The user may enter the profiles 680 using the input/output device 640, such as a keyboard. For example, the profile 680 may include information 690 regarding at least one medication or colorectal cancer classification.

Storing, in step 730, the received levels 670 and the profiles 680 such that each profile 680 is associated with a set of levels 670. The system 600 may store the profiles 680 and the levels 670 in the storage device 630. For example, when the storing is complete, the system 600 can identity a particular one of the profiles 680 that is associated with specific levels 670. Having identified the profile 680, the system 600 can access the information 690 contained within the identified profile 680, as will be described in the following example.

Figure 8:
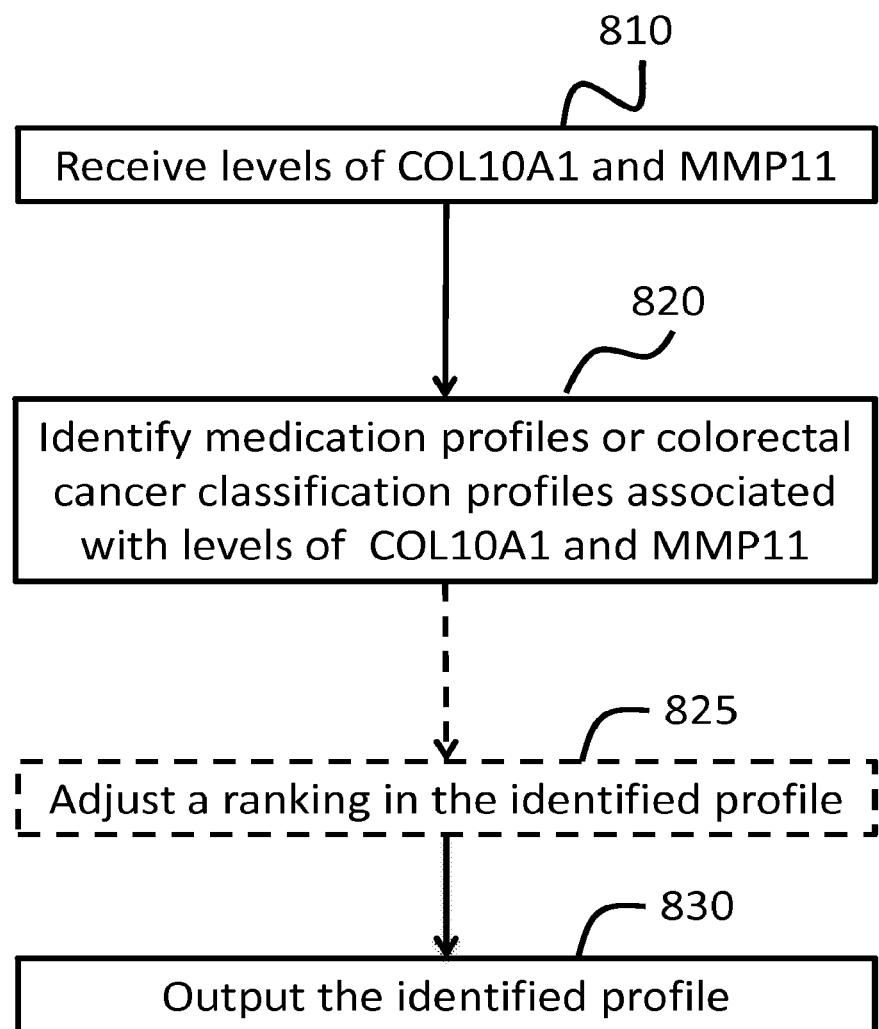
FIG. 8 depicts an exemplary flow chart of a method 300 for selecting medication and/or a colorectal cancer classification for a patient.

The system 600 may be used for selecting a medication or colorectal cancer classification. FIG. 8 shows a flow chart of a method 800 of selecting a medication or colorectal cancer classification for an individual. Preferably, the method 800 is performed in the system 600. For example, a computer program product can include instructions that cause the processor 610 to perform the steps of the method 800. The method 800 includes the following steps.

Receiving, in step 810, an individual's levels of COL10A1 and MMP11. The levels may be entered by a user via input/output device 640. For example, the user may obtain the individual's levels of COL10A1 and MMP11 using the analyzing equipment 660 (which may or may not be connected to the system 600). The user may type the individual's levels on input/output device 640, such as a keyboard, for receipt by the system 600.

The levels may also be received directly from the analyzing equipment 660. For example, analyzing equipment 660 may include a processor and suitable software such that it can communicate over a network. The system 600 may be connected to the analyzing equipment 660 through input/output device 640, such as a network adapter, and directly receive the individual's levels of COL10A1 and MMP11.

Identifying, in step 820, one of the profiles 680 that is associated with the individual's levels of COL10A1 and MMP11. For example, the system 600 may perform a database search in the storage device 630. Particularly, the system 600 may access the levels 670 for individual profiles 680 until a match is found. Optional step 825 will be described below.

Outputting, in step 830, the identified profile 680 in response to receiving the individual's levels of COL10A1 and MMP11. The system may output the identified profile 680 through input/output device 640. For example, the identified profile may be printed or displayed in a suitable graphical user interface on a display device. As another example, the system 600 may transmit the identified profile over a network, such as a local area network or the Internet, to which the input/output device 640 is connected.

The profiles 680 can be created such that there is flexibility in how the system 600 outputs them. For example, the information 690 in one or more of the profiles 680 may include a ranking of several medications or colorectal cancer classifications. The program may include instructions for applying rules to the received individual's levels and adjust the ranking accordingly. In such implementations, the method 800 may include optional step 825 of adjusting the ranking before outputting the identified profile. For example, the system 600 may receive a level of an additional gene correlated with colorectal cancer incidence and/or risk (e.g., ABHD2) and adjust the ranking accordingly in step 825. As another example, step 825 may involve adjusting the ranking based on a clinical response. The clinical response may be received by the system 600 in the same way as the individual's levels. For example, the ranking can be adjusted based on a clinical response by the individual or a member of the individual's family.

The profiles 680 may be updated as necessary. For example, the introduction of a new medication on the market or new information about colorectal cancer may prompt a revision of one or more existing profiles. A new medication may also be the basis for creating a new medication profile. The adjustment or creation of profiles may be done substantially as described above.

The profiles 680 may be used for medication selection and/or colorectal cancer classification in the same system where they were created, or in a different system. That is, the system 600 may first be used for building a database of the profiles 680, and the system 600 may thereafter be used to select a profile for the levels of a specific individual. As another example, one or more profiles 680 may be transmitted within a computer readable medium such as a global computer network for remote processing according to the invention.

EXAMPLES

Example 1: COL10A1 and MMP11 Expression in Colorectal Carcinoma Primary Tumors is Associated with Metastatic Disease Although the UICC staging is an established histopathological categorization system for colorectal carcinomas (CRC) various prognostic subgroups exist within the stages. To guarantee adequate treatment molecular markers maybe helpful to select high or low risk cases during clinical routine. Robust expression and valid identification in routinely asservated material is indispensable as such classifiers.

Patients and Methods

During microarray comparison (Affymetrix, HG-U133A) of 80 fresh frozen CRC samples (stage UICC I, II: n=40 vs. stage UICC III: n=40) 23 genes related to metastases have been identified. Five selected markers (ABHD2, COL10A1, MMP-11, C8orf30A, SLC35D1) were validated by RT-PCR retrospectively (stage UICC I-IV: n=82) and prospectively (stage UICC I-IV: n=155) after RNA isolation by a high throughput platform from routinely harvested FFPE CRC tissues. The marker correlation in the tumor specimens and the correlation of RT-PCR results with immunohistochemistry were compared. The prognostic power was evaluated by multiparametric tests (Bagging, SVM, LDA, Ord-.Log.Reg.)

Results

ABHD2, COL10A1, MMP-11, C8orf30A and SLC35D1 were significantly different expressed in stage UICC I, II vs. III by microarray analysis (p<0.001). Retrospective and prospective RT-PCR validation in FFPE tissue showed that expression of COL10A1 (p=0.001), MMP11 (p=0.006), and ABHD2 (p=0.01) were robustly expressed and significantly associated with metastasis (stage UICC III/IV). Correlation was strongest between COL10A1 and MMP11 with a Spearman's rho value of 0.6-0.82. RT-PCR results did not correlate with immunohistochemistry but follow up in stage UICC II CRC indicated a relation to tumor recurrence. Multiparametric tests identified AUC values between 0.754 (Bagged trees) and 0.795 (SVM).

Conclusion

COL10A1 and MMP11 show a robust and stage dependent expression in CRC primary tumors which is correlated to metastases. They may indicate tumor recurrence after treatment and could therefore act as prognostic profilers to select high risk cases in the future.

Example 2: COL10A1 and MMP11 Expression in Colorectal Carcinoma Primary Tumors Indicates Metastatic Disease The goals of the study were to determine molecular markers which may be used in the primary tumor in order to predict metastatic disease. These markers may be used to detect patients in stage UICC II with high risk for recurrent tumor development after primary therapy and to evaluate the predictive force of single molecular markers against complex multiparameter analysis.

Figure 1F:
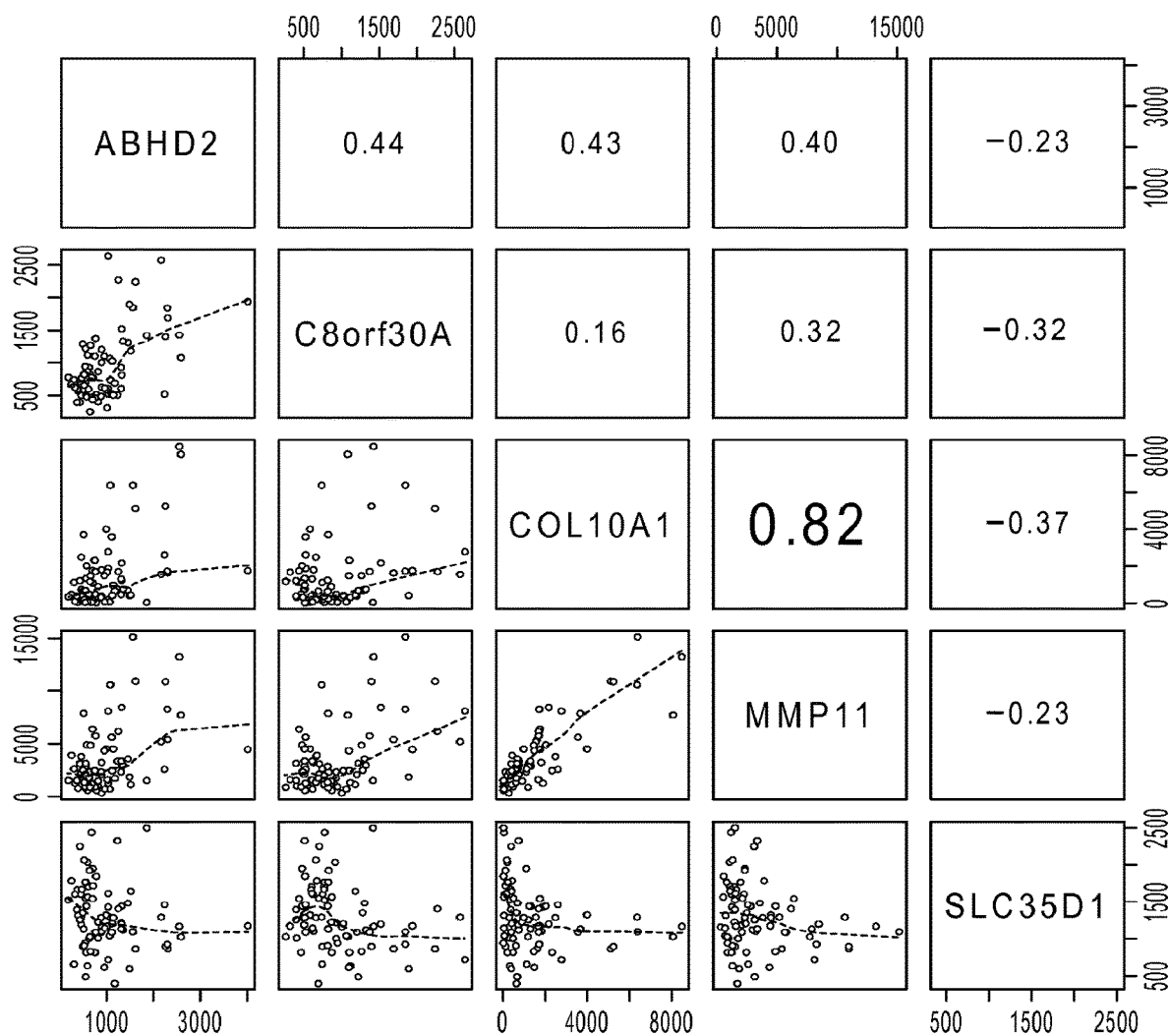

Extraction of markers indicating metastatic colorectal carcinoma from comparative transcriptome analyses Microarray analyses were performed with specimen from primary tumor resections of 80 previously untreated patients with colorectal carcinoma (CRC) (Table 3). Of these patients 40 suffered from tumors in non-metastatic stages UICC I and UICC II and 40 from tumors in the metastatic stage UICC III, respectively. By multivariant biostatistical analyses of the results including the gene expression values a multi-gene panel was extracted, which showed a significant association with the metastatic disease, as reported recently (Croner et al, Ann Surg. 2008; Croner et al., Cancer 2005). From this gene panel three robustly expressed markers were selected for the present study (ABHD2, C8orf30A, SLC35D1). ABHD2 (FIG. 1A) and C8orf30A (FIG. 1D) exhibit increased expression levels in metastatic stages, whereas the expression of SLC35D1 (FIG. 1E) was decreased. The expression level of all three markers was highly significantly different in primary tumors of patients with metastatic as compared to non-metastatic disease (FIG. 1A, D, E). In addition, two further genes were selected by manually rescreening of the microarray results. The selection criteria for these two genes were that they were not identified during multivariate statistics in the previously determined multi-gene panel, but were highly significantly over-expressed in metastatic stages during single value calculations and showed highest expression profiles. The latter criterion was used in order to support an easy detection of these markers in subsequent clinical routine approaches of tumor stage diagnostics. The two best fitting genes to these criteria encoded the collagen variant COL10A1 and the matrix-metalloproteinase 11 (MMP-11). Both genes were in the microarray analysis highly significantly associated with the metastatic tumour stage UICC III (FIG. 1 B, C), but exhibited a clearly higher expression level as compared to the other three markers (FIG. 1, compare B, C vs. A, D, E). In receiver operating characteristic (ROC) analyses area under curve (AUC) values between 0.814 and 0.723 were obtained for the five markers (FIG. 1A-E, right panels). Correlation analyses using scatterplot matrices revealed the strongest correlation between COL10A1 and MMP11 with a Spearman's rho value of 0.82 (FIG. 1F). The correlation of the expression between the other markers was only low or negligible.

TABLE 3

|  | Microarrays | Pilot Study | Validation Cohort (Polyprobe) |
|---|---|---|---|
| n | 80 | 82 | 155 |
| Gender (male:female) | 50:30 | 42:40 | 87:68 |
| Age median (range) | 66 (47-86) | 67 (37-92) | 69 (24-91) |
| Histologic type | | | |
| Adenocarcinoma | 80 | 70 | 145 |
| Mucinous adenocarcinoma | 0 | 12 | 10 |
| pT | | | |
| pT1 | 6 | 7 | 16 |
| pT2 | 19 | 14 | 33 |
| pT3a (≤1 mm) | 14 | 8 | 28 |
| pT3b (>1-≤5 mm) | 13 | 12 | 26 |
| pT3c (>5-15 mm) | 9 | 14 | 14 |
| pT3d (>15 mm) | 1 | 4 | 15 |
| pT3 nos | 2 | 1 | 0 |
| pT4a | 4 | 16 | 17 |
| pT4b | 8 | 6 | 2 |
| pT4c | 0 | 0 | 3 |
| pT4 nos | 4 | 0 | 0 |
| pTx | 0 | 0 | 1 |
| pN | | | |
| pN0 | 40 | 44 | 91 |
| pN1a | 29 | 13 | 18 |
| pN1b | 11 | 11 | 18 |
| pN2a | 0 | 6 | 11 |
| pN2b | 0 | 8 | 17 |
| Distant metastases | | | |
| M0 | 0 | 61 | 122 |
| MIa | 0 | 13 | 19 |
| MIb | 0 | 8 | 14 |
| Stage (UICC 7th ed) | | | |
| IA | 6 | 7 | 15 |
| IB | 11 | 10 | 27 |
| IIA | 19 | 20 | 39 |
| IIB | 4 | 2 | 3 |
| IIC | 0 | 2 | 2 |
| IIIA | 14 | 2 | 5 |
| IIIB | 20 | 12 | 24 |
| IIIC | 6 | 6 | 7 |
| WA | 0 | 13 | 19 |
| WB | 0 | 8 | 14 |
| Lymph invasion | | | |
| L0 | 53 | 49 | 98 |
| L1 | 27 | 33 | 57 |
| Venous invasion | | | |
| V0 | 80 | 77 | 145 |
| V1 | 0 | 5 | 10 |
| Grading | | | |
| Low grade (G1,2) | 65 | 45 | 115 |
| High grade (G3,4) | 15 | 37 | 40 |
| R classification | | | |
| R0 | 80 | 66 | 154 |
| R1 | 0 | 1 | 1 |
| R2 | 0 | 14 | 0 |
| RX | 0 | 1 | 0 |
| Tumor site | | | |
| Coecum | 8 | 14 | 21 |
| Ascending colon | 8 | 17 | 21 |
| Hepatic flexure | 3 | 9 | 7 |
| Transverse colon | 2 | 4 | 18 |
| Splenic flexure | 1 | 2 | 2 |
| Descending colon | 4 | 7 | 6 |
| Sigmoid colon | 20 | 29 | 37 |
| Rectum | 34 | 43 | | nos: not otherwise specified

Figure 2A:
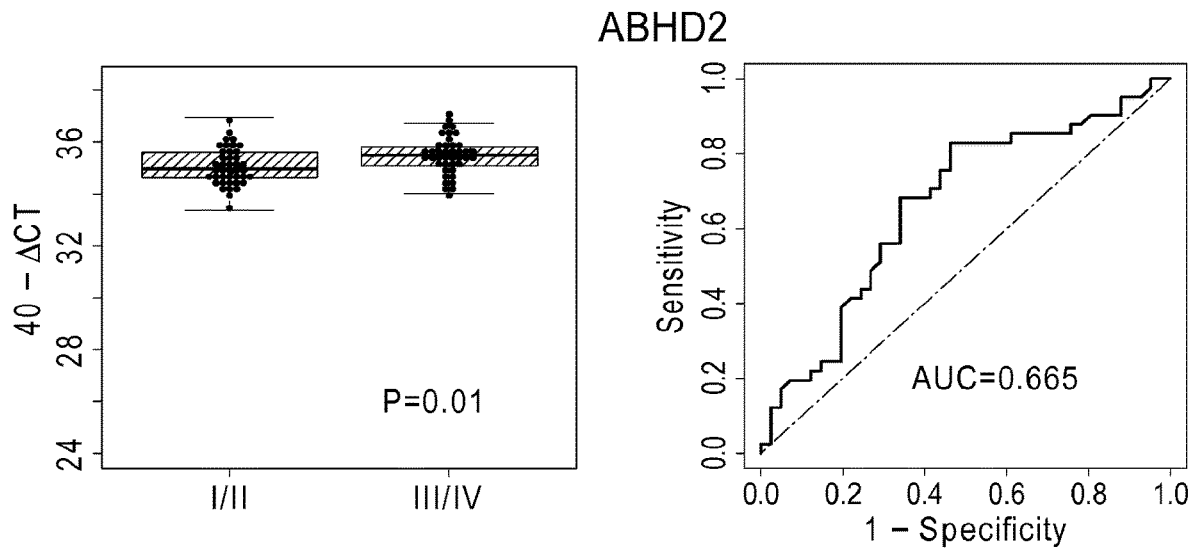
FIGS. 2A-2F shows molecular markers of metastatic CRC as determined by a retrospective analysis using automated RNA extraction from formalin-fixed paraffin-embedded FFPE tissues and quantitative real time polymerase chain reaction (qRT-PCR). Box-plots (Figures A-E, left) and ROC analyses (Figures A-E, right) of gene expression of ABHD2 (A), COL10A1(B), MMP11 (C), C8orf30A (D) and SLC35D1 (E) as determined by microarray analyses. RNA was extracted from 82 patients with primary tumors in different stages [UICC I (n=17), UICC II (n=24), UICC III (n=20), UICC IV (n=21), Table 3]. An automated extraction method for RNA from FFPE tissue sections and subsequent quantitative RT-PCR were applied. P values and AUC are shown. Correlation analyses were carried out using scatterplot matrices and Spearman's rho values (F).
Figure 2B:
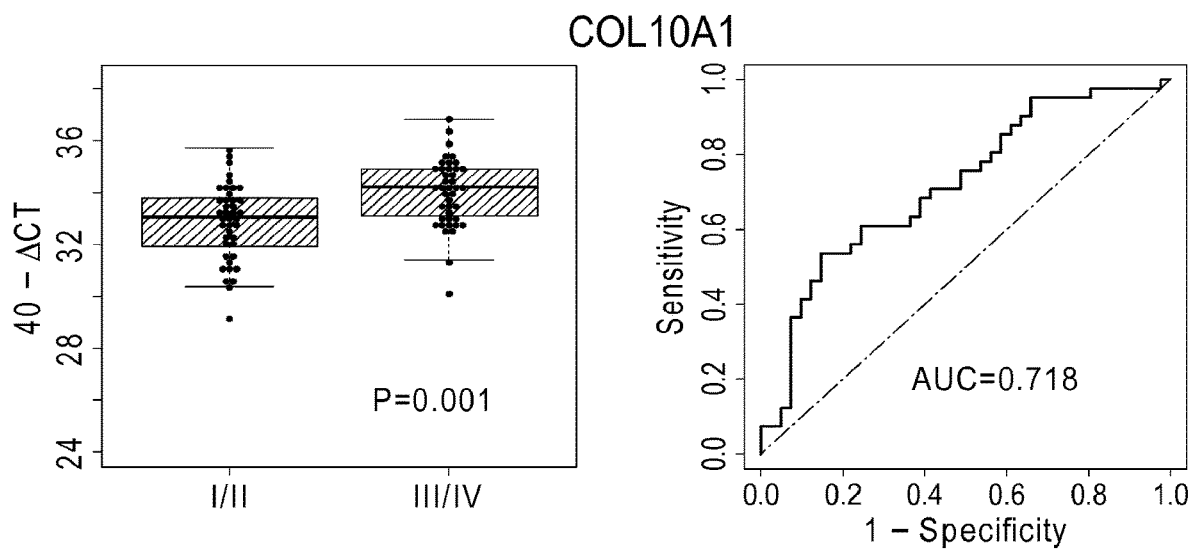
Figure 2C:
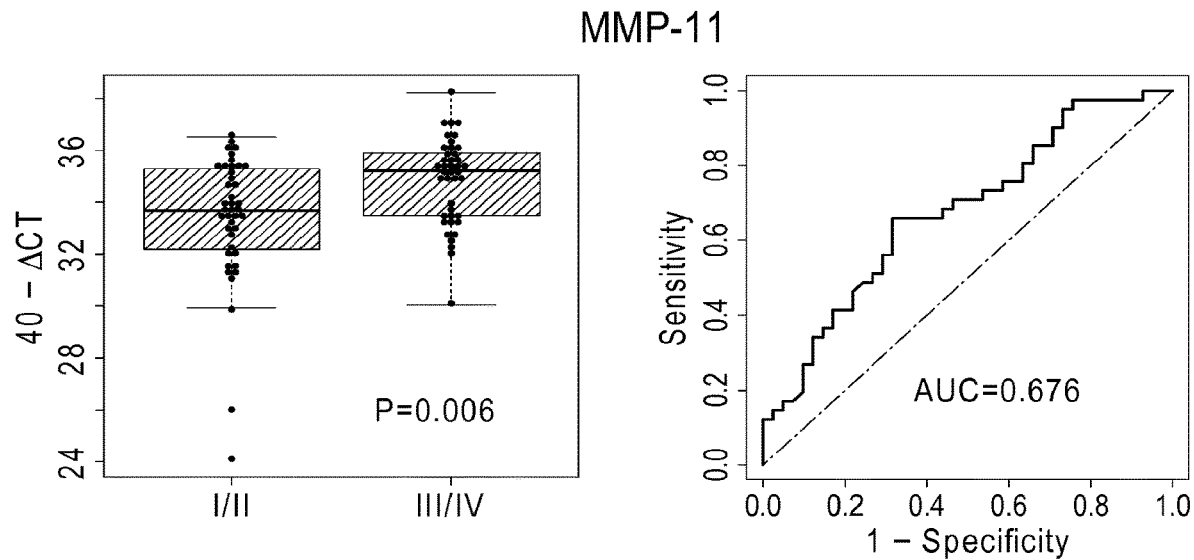
Figure 2D:
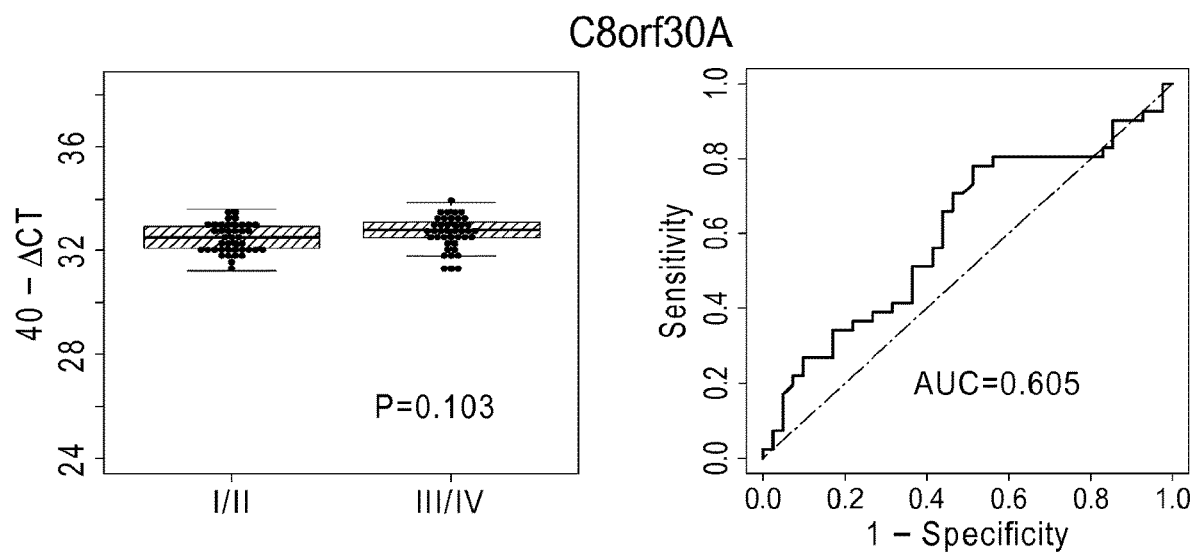
Figure 2E:
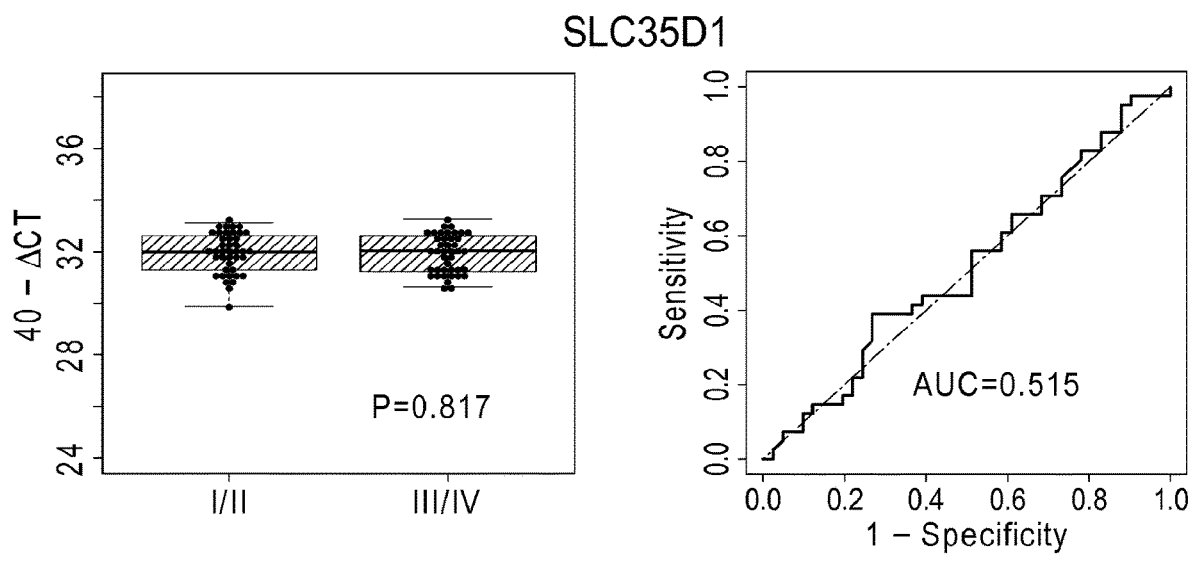
Figure 2F:
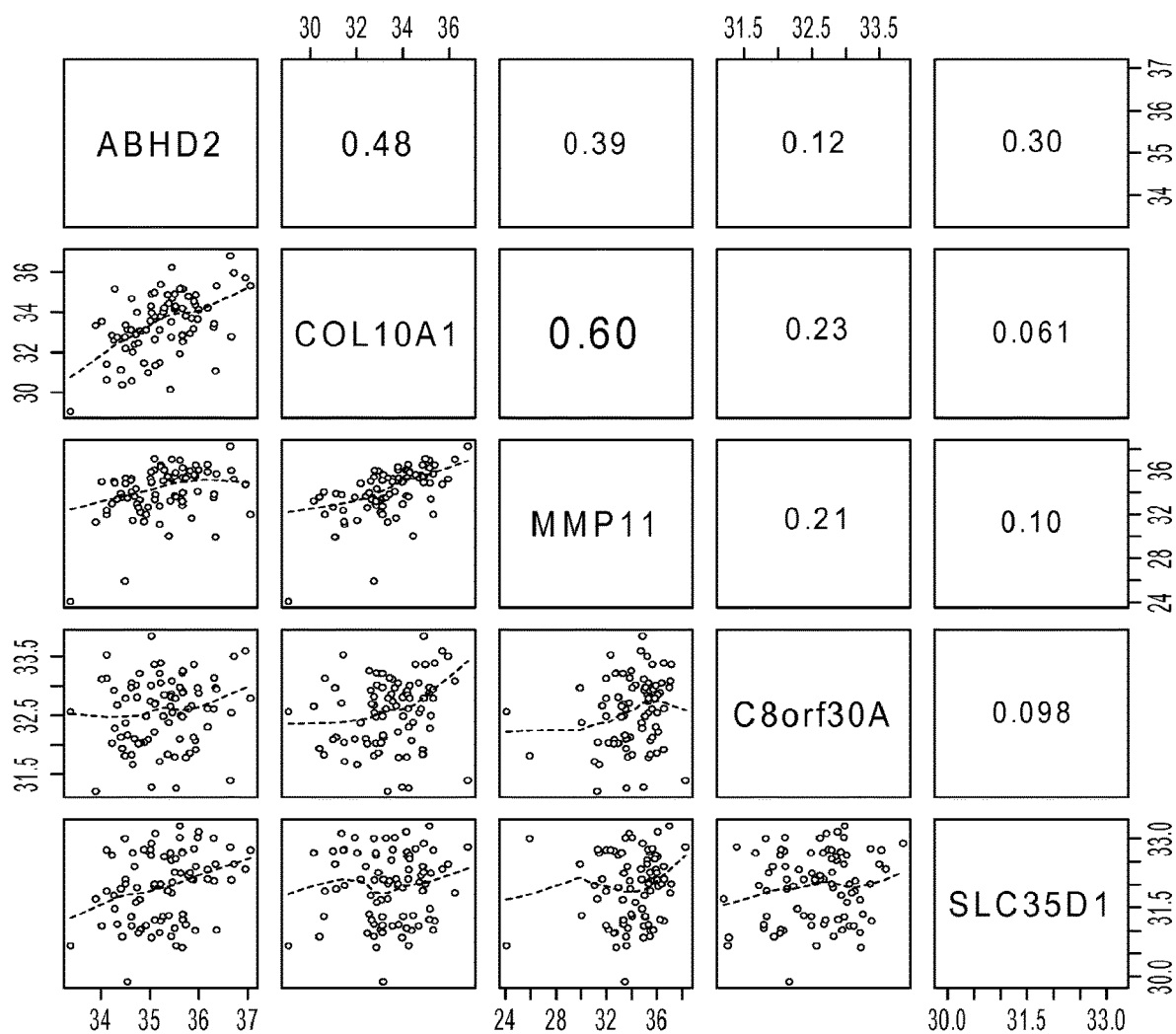

Retrospective Validation of Metastasis Markers Using RNA from Routinely Processed Clinical Specimen In order to validate the five selected markers with a clinically relevant and easily applicable methodology, a retrospective pilot study was carried out including primary CRC tissues from 82 patients in different stages [UICC I (n=17), UICC II (n=24), UICC III (n=20), UICC IV (n=21), Table 3]. An automated extraction method for RNA from FFPE tissue sections and subsequent quantitative RT-PCR were used to determine expression of these marker genes. With this approach, COL10A1 (p=0.001), MMP11 (p=0.006), and ABHD2 (p=0.01) were found to be statistically significantly associated with the metastatic tumor stages (FIG. A-C, left). AUC values of these three markers were between 0.665 and 0.718. The stage related expression of C8orf30A and SLC35D1 could not be confirmed (FIG. 2 D, E). Of note, the expression of C8orf30A and SLC35D1 was clearly lower as the expression of the three other markers (FIG. 2, compare A-C and D, E). As already identified in the microarray analysis the correlation of expression was highest between COL10A1 and MMP11 (FIG. 2F, Spearman's rho=0.60)

Figure 3A:
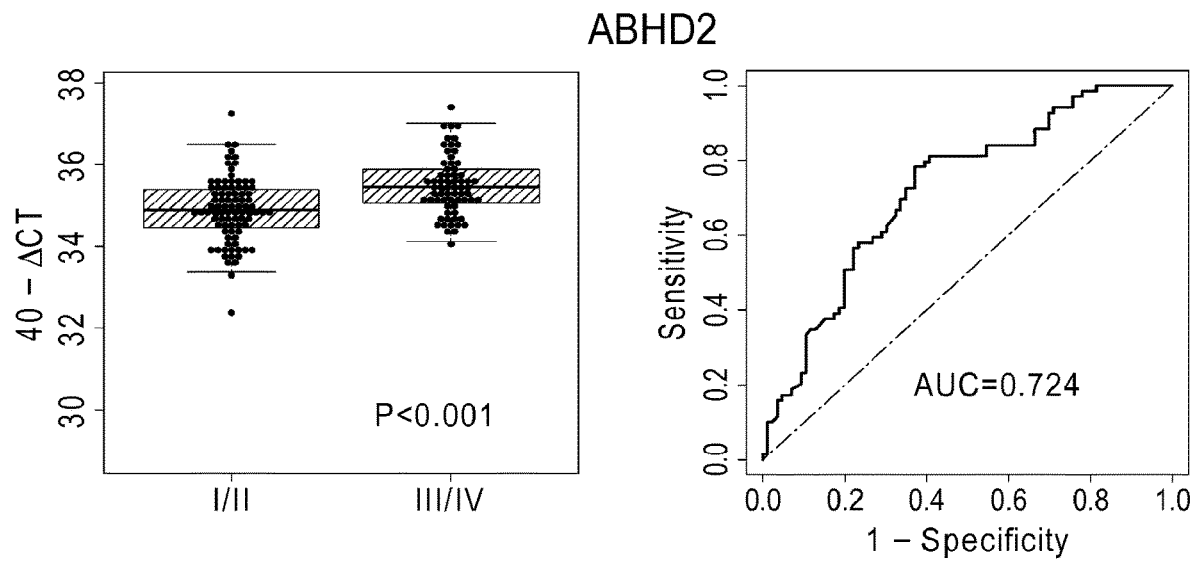
FIGS. 3A-3F shows molecular markers of metastatic CRC as determined by a prospective validation study using automated RNA extraction from FFPE tissues and qRT-PCR. Box-plots (Figures A-E, left) and ROC analyses (Figures A-E, right) of gene expression of ABHD2 (A), COL10A1 (B), MMP11 (C), C8orf30A (D) and SLC35D1 (E) as determined by microarray analyses. RNA was extracted from 153 patients with different stages of colorectal carcinoma [UICC I (n=42), UICC II (n=44), UICC III (n=36), UICC IV (n=33)]. An automated extraction method for RNA from FFPE tissue sections and subsequent quantitative RT-PCR were applied. P values and AUC are shown. Correlation analyses were carried out using scatterplot matrices and Spearman's rho values (F).
Figure 3B:
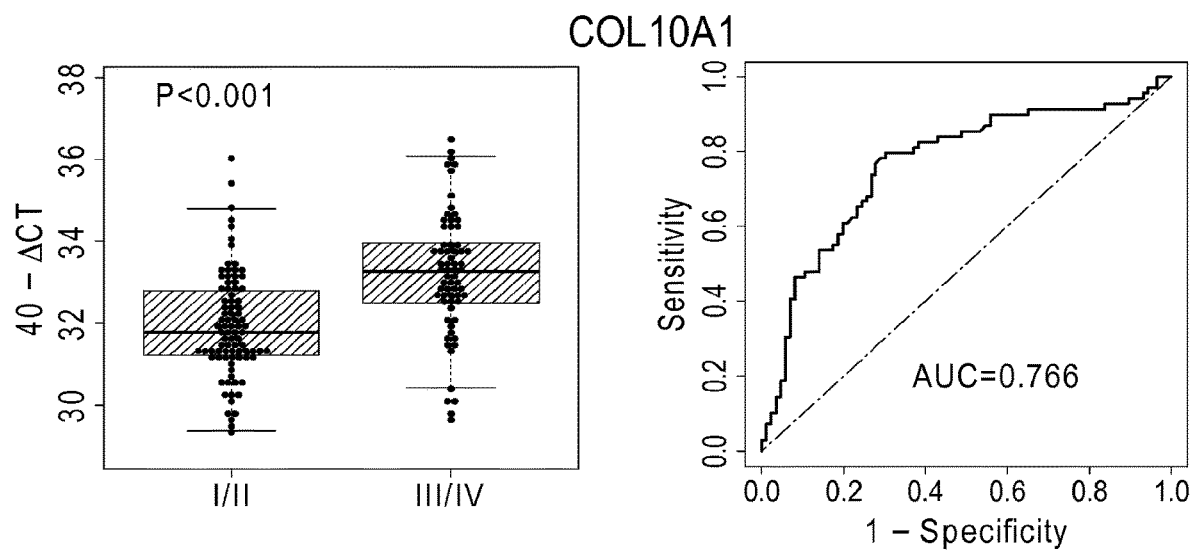
Figure 3C:
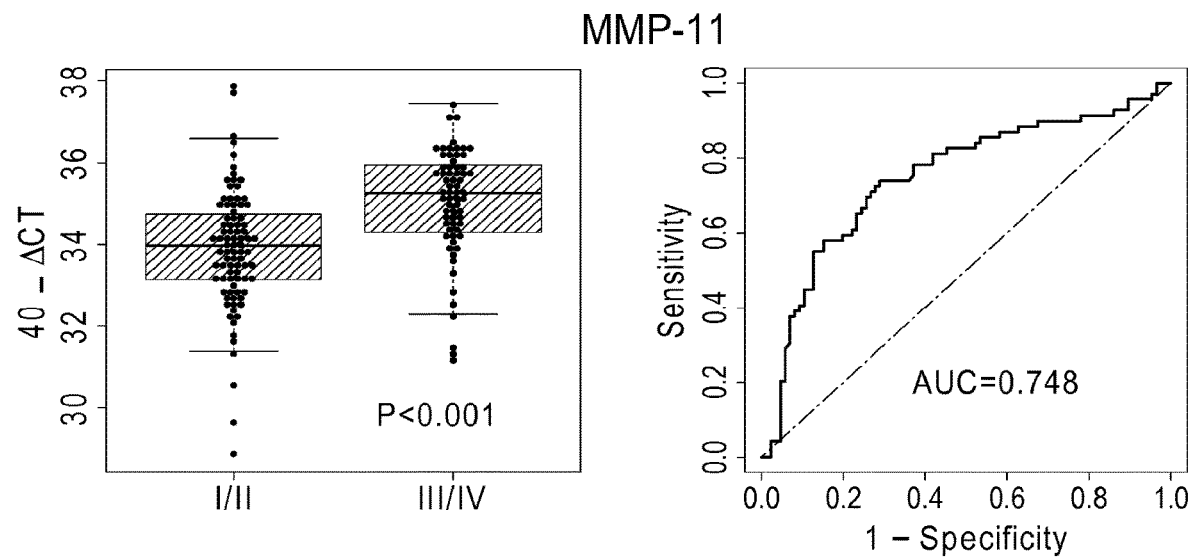
Figure 3D:
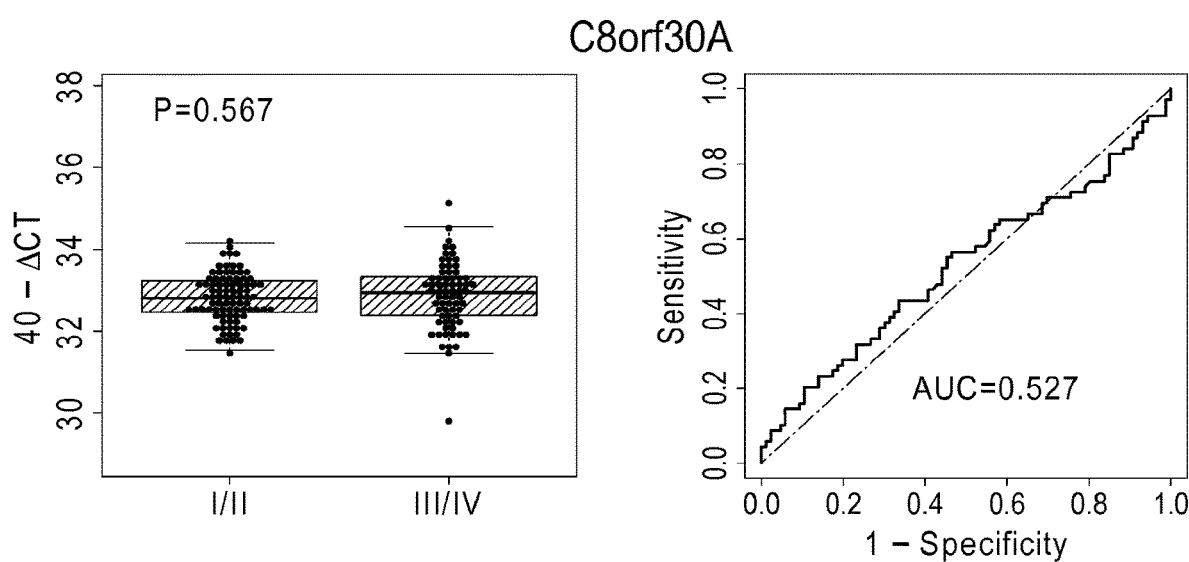
Figure 3E:
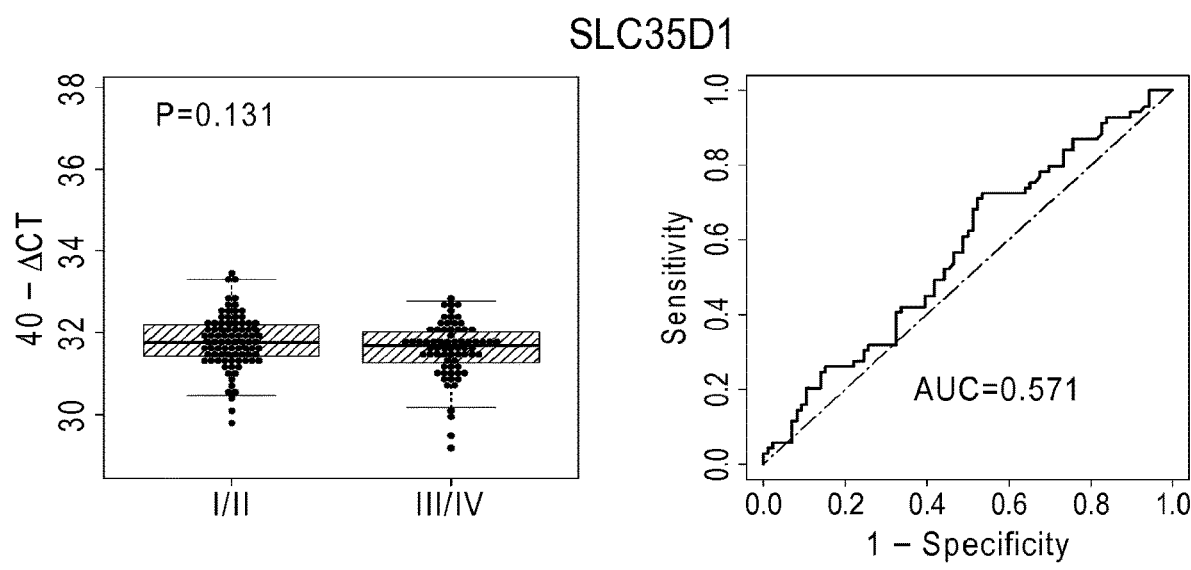
Figure 3F:
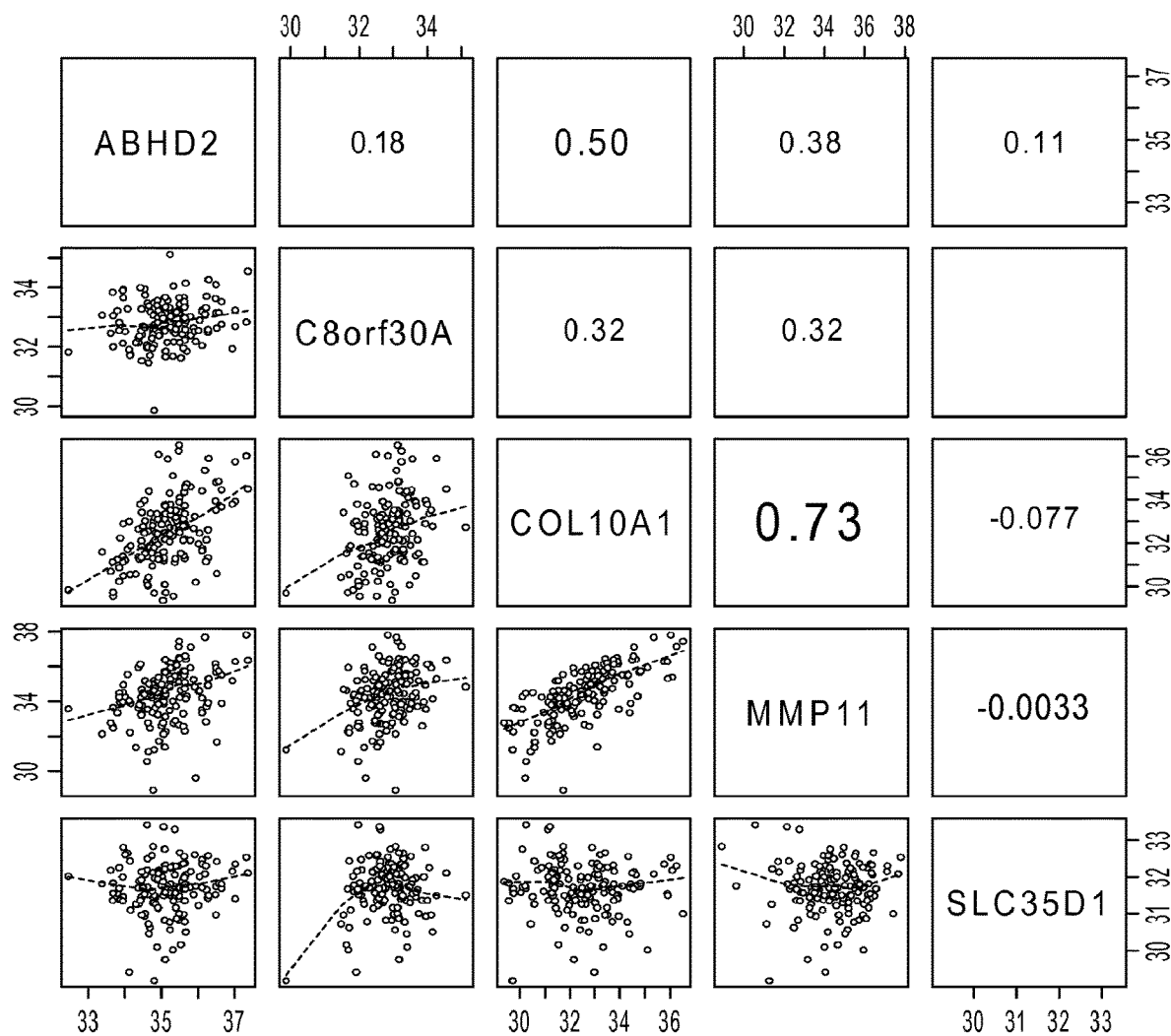

Prospective Validation Study of Metastasis Markers Using Routinely Processed Clinical Specimens In order to unequivocally validate the stage-related expression of the five marker genes a prospective study was carried out including 155 patients with different stages of colorectal carcinoma [UICC I (n=42), UICC II (n=44), UICC III (n=36), UICC IV (n=33)]. As above, the expression of the marker genes was analyzed with RT-PCR using RNA from FPPE-extracted tumor RNA. In this study, the markers ABHD2, COL10A1 and MMP11 could be confirmed to be highly significantly associated with the metastatic stages of colorectal carcinoma (FIG. 3A-C). Again the expression levels of these three genes were higher as compared to C8orf30A and SLC35D1 (FIG. 3, compare A-C vs. D, E). ROC analyses indicated that specificity and sensitivity were highest for COL10A1 (AUC=0.766; FIG. 3B, right) and MMP11 (AUC=0.748; FIG. 3C, left), respectively. Correlation analysis confirmed the close relation of these two markers (FIG. 3F, Spearman's rho=0.73). Moreover, a weak correlation of ABHD2 and COL10A1 was noticed (FIG. 3F, Spearman's rho=0.50).

COL10A1 and MMP11 indicate increased risk of disease recurrence in UICC II stage patients From these results, COL10A1 and MMP11 were identified as being the best markers in order to predict metastasis via gene expression in CRC primary tumors. Graphical display of the expression levels of the two genes in all of the different tumors from FFPE tissue of the prospective validation study demonstrated that high expression is preferentially associated with metastatic stages (FIG. 4A, B) and low expression with non-metastatic (FIG. 4A, B) stages of CRC.

Figure 4A:
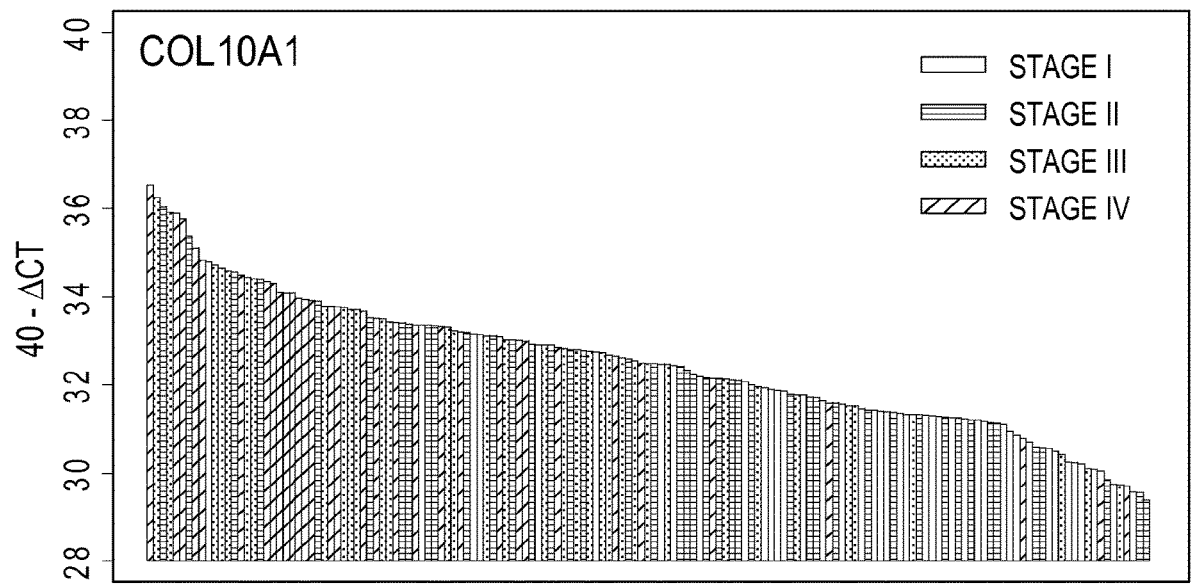
FIGS. 4A-4D shows stage related expression and association to recurrence in stage UICC II CRC of COL10A1 and MMP11. Waterfall plots of expression and stage are given for COL10A1 (A) and MMP11 (B). Tumor stages are indicated. Expression of COL10A1 (C) and MMP11 (D) in 20 patients of stage UICC II as determined by microarray analysis and in relation to the development of distant metastasis after primary treatment during the follow up period. Patients with recurrent disease (relapse) are indicated.
Figure 4B:
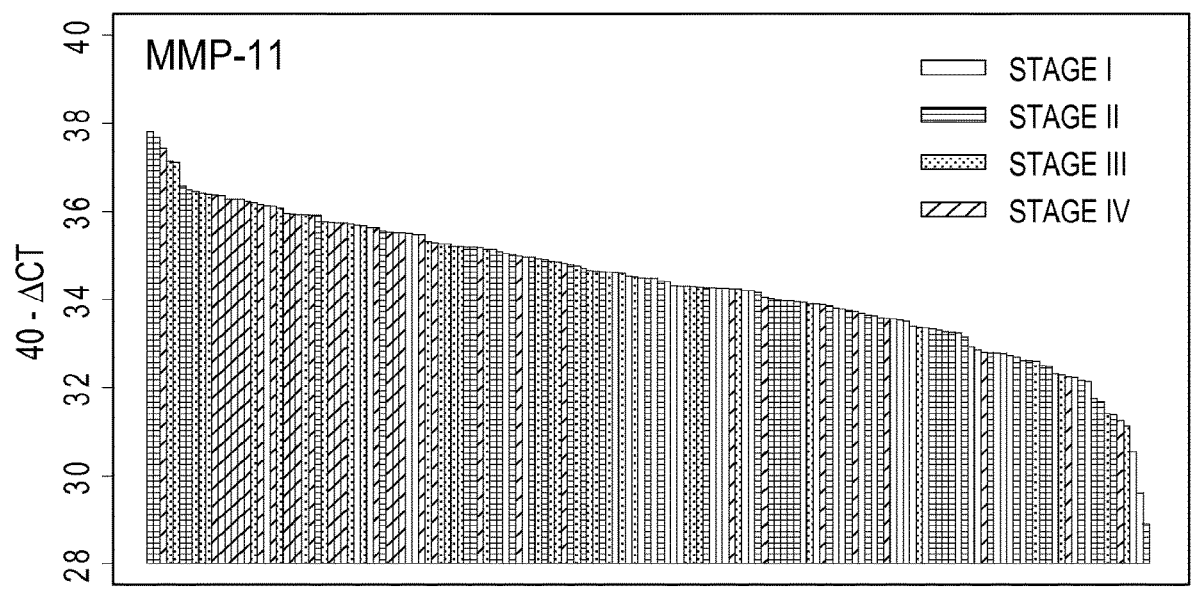
Figure 4C:
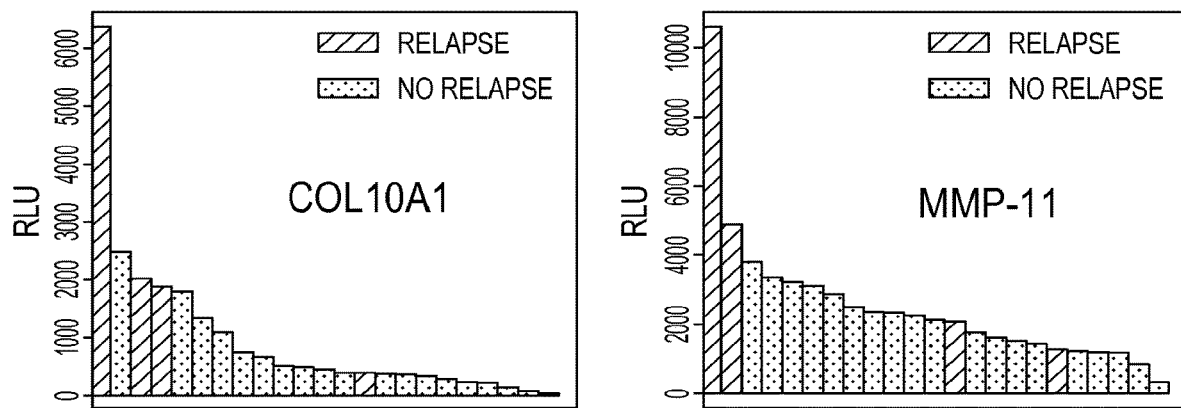
Figure 4D:
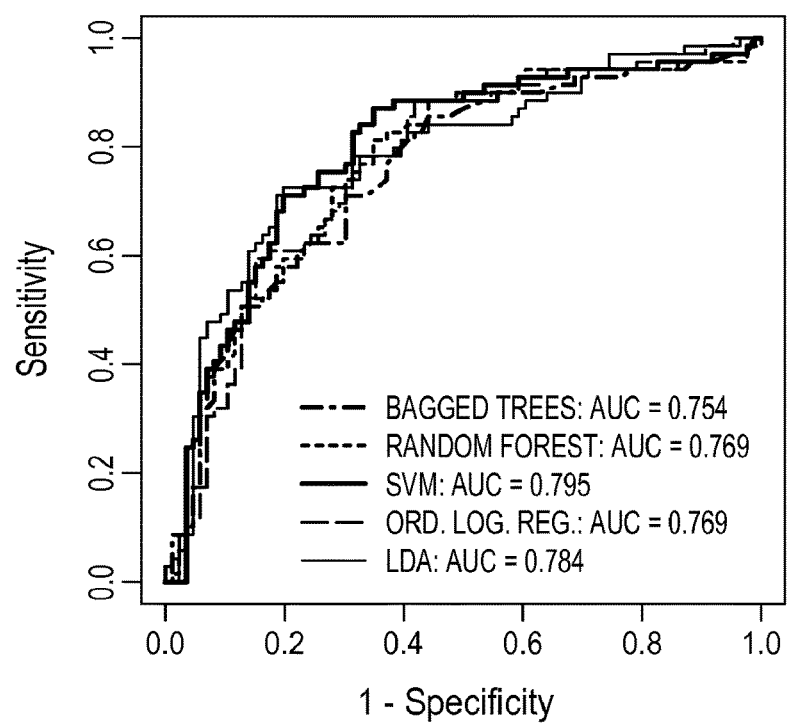

However, this graphical display also showed that some tumors with putatively non-metastatic stage UICC II showed high expression of these genes (FIG. 4A, B; asterisks). This may indicate increased risk of tumor recurrence of the disease in these cases (FIG. 4A, B). Due to the fact that follow up time of the prospective validation study was too short to identify recurrent tumors, this hypothesis was analyzed using the UICC II stage patients from the microarray cohort. Of note, most of those patients with tumor recurrence showed originally a high expression level of either COL10A1 or MMP11 in the primary tumor (FIG. 4C). Finally whether different multiparametric tests (Bagging, SVM, LDA, Ord.Log.Reg.) including all of the five markers may confirm the predictive power of these markers was investigated. In these analyses, AUC values between 0.754 (Bagged trees) and 0.795 (SVM) were determined (FIG. 4D). These analyses confirmed with an unbiased statistical tests the great values of the selected marker panel.

Predictive Force of COL10A1 and MMP11 is Selectively Exhibited at the RNA Level

Figure 5A:
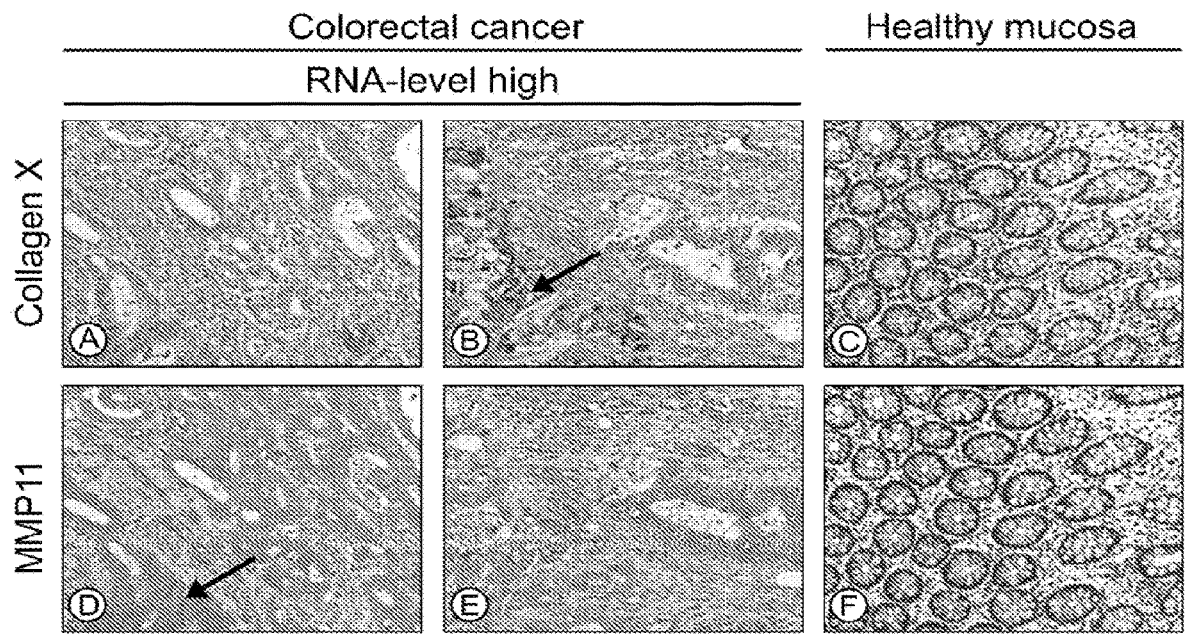
FIG. 5A contains panels A-F, and FIG. 5B contains panels G-L.
Figure 5B:
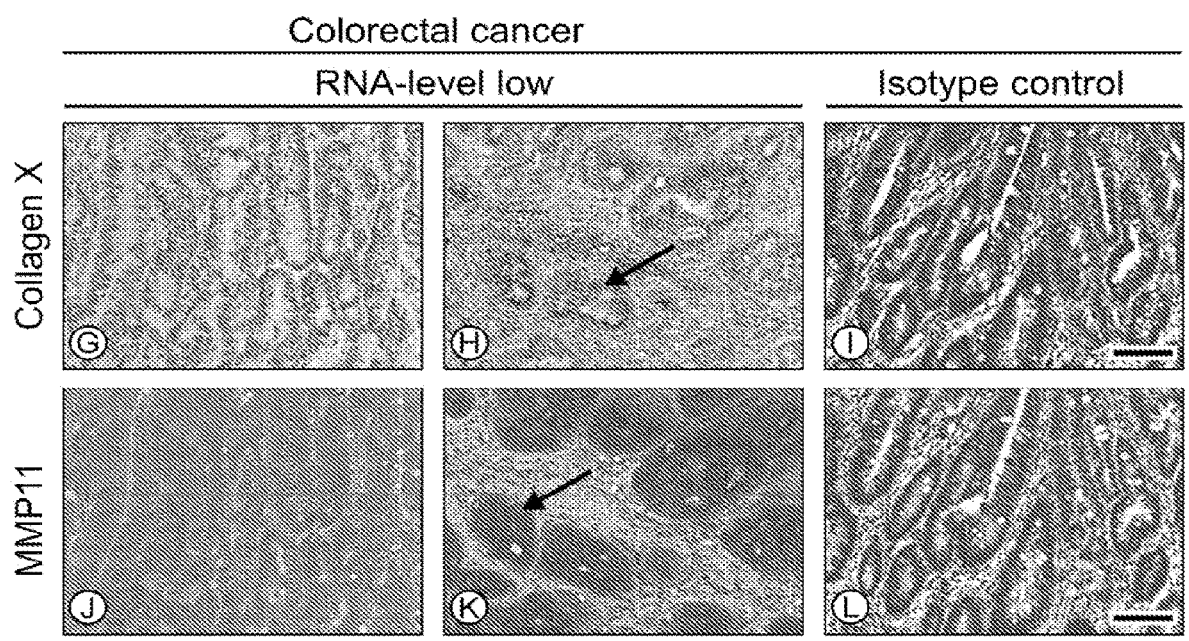

The gene products of COL10A1 and MMP11 are both secreted proteins. Accordingly protein levels may vary in different tumors in a not tumor stages related manner due to different secretion modalities and intratumoral deposition of the proteins. Accordingly, the detection of the respective proteins may not be related to the tumor stage as compared to RNA. In order to investigate this, twelve CRC specimens were selected which exhibited either high (n=6) or a low (n=6) expression of COL10A1 (Table 4, low expression COL10A1 P1-P6; high expression P7-P12). As expected the expression of MMP11 RNA correlated well with the COL10A1 RNA (Table 4). Immunohistochemical detection of both proteins on serial sections showed that both proteins were present in higher amounts in the tumor tissues (FIG. 5A, panels A, B, D, and E, and FIG. 5B, panels G, H, J, and K) as compared to the normal colon tissues of the same patients (FIG. 5A, panels C and F). However, proteins levels of both markers were neither related to the RNA level (Table 4) nor with each other (FIG. 5A, compare panels A, B and D, E; Table 4). These findings demonstrated that the two markers are validly associated with metastatic disease at the RNA level only, but not at the protein level.

TABLE 4

| Staining | Patient ID | qRT-PCR (40-ΔCT) | Immunohistochemistry (cell count/intensity) |
|---|---|---|---|
| COL10A1 | | | |
| | P1 | 29.05 | 3/+++ |
| | P2 | 31.07 | — |
| | P3 | 31.48 | — |
| | P4 | 32.75 | — |
| | P5 | 32.77 | 1/+ |
| | P6 | 32.94 | — |
| | P7 | 35.14 | — |
| | P8 | 35.19 | 1/+ |
| | P9 | 35.31 | 2/++ |
| | P10 | 35.37 | 1/++ |
| | P11 | 35.71 | 1/+ |
| | P12 | 36.24 | 1/++ |
| MMP11 | | | |
| | P1 | 24.08 | 3/+++ |
| | P2 | 29.93 | 2/++ |
| | P3 | 31.08 | 3/+++ |
| | P9 | 31.99 | 2/+ |
| | P8 | 33.38 | 2/++ |
| | P11 | 34.72 | 3/+++ |
| | P4 | 35.43 | 2/+++ |
| | P6 | 36 | 2/++ |
| | P5 | 36.02 | 3/+++ |
| | P7 | 36.26 | 3/+++ |
| | P10 | 36.53 | 3/+ |
| | P12 | 37.03 | 2/+ |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

What is claimed is:

1. A method for generating a transcriptome profile in a sample from an individual suffering from or at risk of colorectal cancer, the method comprising:
    (i) in the sample, measuring a level of RNA corresponding to a ABHD2 gene and a level of RNA corresponding to
        (a) a COL10A1 gene,
        (b) a MMP11 gene, or
        (c) both (a) and (b); and
    (ii) determining a difference between the measured level of RNA corresponding to the ABHD2 gene and an ABHD2 threshold level, and
        (a) determining a difference between the measured level of RNA corresponding to the COL10A gene and an COL10A threshold level,
        (b) determining a difference between the measured level of RNA corresponding to the MMP11 gene and an MMP11 threshold level, or
        (c) both (a) and (b); and
    (iii) generating a transcriptome profile based on the differences determined in (ii).

2. The method of claim 1, wherein the individual has colorectal cancer in stage UICC I or stage UICC II.

3. The method of claim 1, wherein the individual is a human and the sample comprises human tumor tissue.

4. The method of claim 1, wherein the sample is obtained from a primary colorectal tumor.

5. The method of claim 1, wherein measuring the level of RNA corresponding to a ABHD2 gene includes performing a northern analysis, a semi-quantitative reverse transcriptase PCR, a quantitative reverse transcriptase PCR, and/or a microarray analysis.

6. The method of claim 1, wherein measuring the level of RNA corresponding to (a) a COL10A1 gene, (b) a MMP11 gene, or (c) both (a) and (b) includes performing a northern analysis, a semi-quantitative reverse transcriptase PCR, a quantitative reverse transcriptase PCR, and/or a microarray analysis.

7. The method of claim 1, wherein determining a difference between:
    (1) the measured level of RNA corresponding to the ABHD2 gene and an ABHD2 threshold level,
    (2) the measured level of RNA corresponding to the COL10A gene and an COL10A threshold level,
    (3) the measured level of RNA corresponding to the MMP11 gene and an MMP11 threshold level, or
    (4) any combination of (1), (2), and (3),
    comprises determining a percent difference.

8. The method of claim 1, wherein the generated transcriptome profile indicates when the measured level of RNA transcribed from the ABHD2 gene is increased 10% or more relative to the ABHD2 threshold level.

9. The method of claim 1, wherein the generated transcriptome profile indicates when the measured level of RNA transcribed from the COL10A1 gene is increased 10% or more relative to the COL10A1 threshold level, the measured level of RNA transcribed from the MMP11 gene is increased 10% or more relative to a MMP11 threshold level, or both.

10. The method of claim 1, wherein the generated transcriptome profile indicates when the measured level of RNA transcribed from the ABHD2 gene is increased 25% or more relative to the ABHD2 threshold level.

11. The method of claim 1, wherein the generated transcriptome profile indicates when the measured level of RNA transcribed from the COL10A1 gene is increased 25% or more relative to the COL10A1 threshold level, the measured level of RNA transcribed from the MMP11 gene is increased 25% or more relative to a MMP11 threshold level, or both.

12. The method of claim 1, wherein the ABHD2 threshold level comprises a historical reference level of RNA transcribed from the ABHD2 gene.

13. The method of claim 1, wherein the COL10A1 threshold level comprises a historical reference level of RNA transcribed from the COL10A1 gene.

14. The method of claim 1, wherein the MMP11 threshold level comprises a historical reference level of RNA transcribed from the MMP11 gene.

15. The method of claim 1, wherein the ABHD2 threshold level comprises a level of RNA transcribed from the ABHD2 gene in a sample from an individual with a known risk or incidence of colorectal cancer.

16. The method of claim 1, wherein the COL10A1 threshold level comprises a level of RNA transcribed from the COL10A1 gene in a sample from an individual with a known risk or incidence of colorectal cancer.

17. The method of claim 1, wherein the MMP11 threshold level comprises a level of RNA transcribed from the MMP11 gene in a sample from an individual with a known risk or incidence of colorectal cancer.

* * * * *

SEQUENCE LISTING

```
<160> NUMBER OF SEQ ID NOS: 4

<210> SEQ ID NO 1
<211> LENGTH: 680
<212> TYPE: PRT
<213> ORGANISM: Homo sapiens

<400> SEQUENCE: 1

Met Leu Pro Gln Ile Pro Phe Leu Leu Leu Val Ser Leu Asn Leu Val
1               5                   10                  15

His Gly Val Phe Tyr Ala Glu Arg Tyr Gln Met Pro Thr Gly Ile Lys
                20                  25                  30

Gly Pro Leu Pro Asn Thr Lys Thr Gln Phe Phe Ile Pro Tyr Thr Ile
                35                  40                  45

Lys Ser Lys Gly Ile Ala Val Arg Gly Glu Gln Gly Thr Pro Gly Pro
    50                  55                  60

Pro Gly Pro Ala Gly Pro Arg Gly His Pro Gly Pro Ser Gly Pro Pro
65                  70                  75                  80

Gly Lys Pro Gly Tyr Gly Ser Pro Gly Leu Gln Gly Glu Pro Gly Leu
                85                  90                  95

Pro Gly Pro Pro Gly Pro Ser Ala Val Gly Lys Pro Gly Val Pro Gly
                100                 105                 110

Leu Pro Gly Lys Pro Gly Glu Arg Gly Pro Tyr Gly Pro Lys Gly Asp
                115                 120                 125

Val Gly Pro Ala Gly Leu Pro Gly Pro Arg Gly Pro Pro Gly Pro Pro
                130                 135                 140
```

```
Gly Ile Pro Gly Pro Ala Gly Ile Ser Val Pro Gly Lys Pro Gly Gln
145                 150                 155                 160

Gln Gly Pro Thr Gly Ala Pro Gly Pro Arg Gly Phe Pro Gly Glu Lys
            165                 170                 175

Gly Ala Pro Gly Val Pro Gly Met Asn Gly Gln Lys Gly Glu Met Gly
            180                 185                 190

Tyr Gly Ala Pro Gly Arg Pro Gly Glu Arg Gly Leu Pro Gly Pro Gln
            195                 200                 205

Gly Pro Thr Gly Pro Ser Gly Pro Pro Gly Val Gly Lys Arg Gly Glu
    210                 215                 220

Asn Gly Val Pro Gly Gln Pro Gly Ile Lys Gly Asp Arg Gly Phe Pro
225                 230                 235                 240

Gly Glu Met Gly Pro Ile Gly Pro Pro Gly Pro Gln Gly Pro Pro Gly
            245                 250                 255

Glu Arg Gly Pro Glu Gly Ile Gly Lys Pro Gly Ala Ala Gly Ala Pro
            260                 265                 270

Gly Gln Pro Gly Ile Pro Gly Thr Lys Gly Leu Pro Gly Ala Pro Gly
    275                 280                 285

Ile Ala Gly Pro Pro Gly Pro Pro Gly Phe Gly Lys Pro Gly Leu Pro
290                 295                 300

Gly Leu Lys Gly Glu Arg Gly Pro Ala Gly Leu Pro Gly Gly Pro Gly
305                 310                 315                 320

Ala Lys Gly Glu Gln Gly Pro Ala Gly Leu Pro Gly Lys Pro Gly Leu
            325                 330                 335

Thr Gly Pro Pro Gly Asn Met Gly Pro Gln Gly Pro Lys Gly Ile Pro
            340                 345                 350

Gly Ser His Gly Leu Pro Gly Pro Lys Gly Glu Thr Gly Pro Ala Gly
            355                 360                 365

Pro Ala Gly Tyr Pro Gly Ala Lys Gly Glu Arg Gly Ser Pro Gly Ser
    370                 375                 380

Asp Gly Lys Pro Gly Tyr Pro Gly Lys Pro Gly Leu Asp Gly Pro Lys
385                 390                 395                 400

Gly Asn Pro Gly Leu Pro Gly Pro Lys Gly Asp Pro Gly Val Gly Gly
            405                 410                 415

Pro Pro Gly Leu Pro Gly Pro Val Gly Pro Ala Gly Ala Lys Gly Met
            420                 425                 430

Pro Gly His Asn Gly Glu Ala Gly Pro Arg Gly Ala Pro Gly Ile Pro
            435                 440                 445

Gly Thr Arg Gly Pro Ile Gly Pro Pro Gly Ile Pro Gly Phe Pro Gly
    450                 455                 460

Ser Lys Gly Asp Pro Gly Ser Pro Gly Pro Pro Gly Pro Ala Gly Ile
465                 470                 475                 480

Ala Thr Lys Gly Leu Asn Gly Pro Thr Gly Pro Pro Gly Pro Pro Gly
            485                 490                 495

Pro Arg Gly His Ser Gly Glu Pro Gly Leu Pro Gly Pro Pro Gly Pro
            500                 505                 510

Pro Gly Pro Pro Gly Gln Ala Val Met Pro Glu Gly Phe Ile Lys Ala
            515                 520                 525

Gly Gln Arg Pro Ser Leu Ser Gly Thr Pro Leu Val Ser Ala Asn Gln
    530                 535                 540

Gly Val Thr Gly Met Pro Val Ser Ala Phe Thr Val Ile Leu Ser Lys
545                 550                 555                 560

Ala Tyr Pro Ala Ile Gly Thr Pro Ile Pro Phe Asp Lys Ile Leu Tyr
```

```
            565                 570                 575
Asn Arg Gln Gln His Tyr Asp Pro Arg Thr Gly Ile Phe Thr Cys Gln
            580                 585                 590

Ile Pro Gly Ile Tyr Tyr Phe Ser Tyr His Val His Val Lys Gly Thr
            595                 600             605

His Val Trp Val Gly Leu Tyr Lys Asn Gly Thr Pro Val Met Tyr Thr
        610             615                 620

Tyr Asp Glu Tyr Thr Lys Gly Tyr Leu Asp Gln Ala Ser Gly Ser Ala
625                 630                 635                 640

Ile Ile Asp Leu Thr Glu Asn Asp Gln Val Trp Leu Gln Leu Pro Asn
                645                 650                 655

Ala Glu Ser Asn Gly Leu Tyr Ser Ser Glu Tyr Val His Ser Ser Phe
            660                 665                 670

Ser Gly Phe Leu Val Ala Pro Met
            675                 680

<210> SEQ ID NO 2
<211> LENGTH: 3352
<212> TYPE: DNA
<213> ORGANISM: Homo sapiens

<400> SEQUENCE: 2
```

| | | | | | |
|---|---|---|---|---|---|
| aaatgctgag | ctaggggcag | gaggcatggg | cgggacagtg | ttctgcacct | tctgcactgc | 60 |
| tcatctgggc | agaggaagct | tcagaaagct | gccaaggcac | catctccagg | aactcccagc | 120 |
| acgcagaatc | catctgagaa | tatgctgcca | caaatacccct | ttttgctgct | agtatccttg | 180 |
| aacttggttc | atggagtgtt | ttacgctgaa | cgataccaaa | tgcccacagg | cataaaaggc | 240 |
| ccactaccca | acaccaagac | acagttcttc | attccctaca | ccataaagag | taaaggtata | 300 |
| gcagtaagag | gagagcaagg | tactcctggt | ccaccaggcc | ctgctggacc | tcgagggcac | 360 |
| ccaggtcctt | ctggaccacc | aggaaaacca | ggctacggaa | gtcctggact | ccaaggagag | 420 |
| ccagggttgc | caggaccacc | gggaccatca | gctgtaggga | accaggtgt | gccaggactc | 480 |
| ccaggaaaac | caggagagag | aggaccatat | ggaccaaaag | gagatgttgg | accagctggc | 540 |
| ctaccaggac | cccggggccc | accaggacca | cctggaatcc | ctggaccggc | tggaatttct | 600 |
| gtgccaggaa | aacctggaca | cagggaccc | acaggagccc | caggacccag | gggctttcct | 660 |
| ggagaaaagg | gtgcaccagg | agtccctggt | atgaatggac | agaaagggga | aatgggtat | 720 |
| ggtgctcctg | gtcgtccagg | tgagaggggt | cttccaggcc | tcagggtcc | cacaggacca | 780 |
| tctggccctc | ctggagtggg | aaaaagaggt | gaaaatgggg | ttccaggaca | gccaggcatc | 840 |
| aaaggtgata | gaggttttcc | gggagaaatg | ggaccaattg | gcccaccagg | tccccaaggc | 900 |
| cctcctgggg | aacgagggcc | agaaggcatt | ggaaagccag | gagctgctgg | agccccaggc | 960 |
| cagccaggga | ttccaggaac | aaaaggtctc | cctggggctc | caggaatagc | tgggccccca | 1020 |
| gggcctcctg | gctttgggaa | accaggcttg | ccaggcctga | aggagaaag | aggacctgct | 1080 |
| ggccttcctg | ggggtccagg | tgccaaaggg | gaacaagggc | cagcaggtct | tcctgggaag | 1140 |
| ccaggtctga | ctggaccccc | tggaaatatg | ggacccaag | gaccaaaagg | catcccgggt | 1200 |
| agccatggtc | tcccaggccc | taaggtgag | acagggccca | ctgggcctgc | aggatacct | 1260 |
| ggggctaagg | gtgaaagggg | ttcccctggg | tcagatggaa | aaccagggta | cccaggaaaa | 1320 |
| ccaggtctcg | atggtcctaa | gggtaaccca | gggttaccag | gtccaaaagg | tgatcctgga | 1380 |
| gttggaggac | ctcctggtct | cccaggccct | gtgggcccag | caggagcaaa | gggaatgccc | 1440 |

-continued

| | |
|---|---|
| ggacacaatg gagaggctgg cccaagaggt gcccctggaa taccaggtac tagaggccct | 1500 |
| attgggccac caggcattcc aggattccct gggtctaaag gggatccagg aagtcccggt | 1560 |
| cctcctggcc cagctggcat agcaactaag ggcctcaatg gacccaccgg gccaccaggg | 1620 |
| cctccaggtc caagaggcca ctctggagag cctggtcttc cagggccccc tgggcctcca | 1680 |
| ggcccaccag gtcaagcagt catgcctgag ggttttataa aggcaggcca aaggcccagt | 1740 |
| ctttctggga cccctcttgt tagtgccaac caggggtaa caggaatgcc tgtgtctgct | 1800 |
| tttactgtta ttctctccaa agcttaccca gcaataggaa ctcccatacc atttgataaa | 1860 |
| attttgtata acaggcaaca gcattatgac ccaaggactg gaatctttac ttgtcagata | 1920 |
| ccaggaatat actattttc ataccacgtg catgtgaaag ggactcatgt ttgggtaggc | 1980 |
| ctgtataaga atggcacccc tgtaatgtac acctatgatg aatacaccaa aggctacctg | 2040 |
| gatcaggctt cagggagtgc catcatcgat ctcacagaaa atgaccaggt gtggctccag | 2100 |
| cttcccaatg ccgagtcaaa tggcctatac tcctctgagt atgtccactc ctctttctca | 2160 |
| ggattcctag tggctccaat gtgagtacac acagagctaa tctaaatctt gtgctagaaa | 2220 |
| aagcattctc taactctacc ccaccctaca aaatgcatat ggaggtaggc tgaaaagaat | 2280 |
| gtaatttta ttttctgaaa tacagatttg agctatcaga ccaacaaacc ttcccctga | 2340 |
| aaagtgagca gcaacgtaaa aacgtatgtg aagcctctct tgaatttcta gttagcaatc | 2400 |
| ttaaggctct ttaaggtttt ctccaatatt aaaaaatatc accaagaag tcctgctatg | 2460 |
| ttaaaaacaa acaacaaaaa acaaacaaca aaaaaaaaat taaaaaaaaa aacagaaata | 2520 |
| gagctctaag ttatgtgaaa tttgatttga gaaactcggc attcctttt taaaaaagcc | 2580 |
| tgtttctaac tatgaatatg agaacttcta ggaaacatcc aggaggtatc atataacttt | 2640 |
| gtagaactta aatacttgaa tattcaaatt taaaagacac tgtatcccct aaaatatttc | 2700 |
| tgatggtgca ctactctgag gcctgtatgg cccctttcat caatatctat tcaaatatac | 2760 |
| aggtgcatat atacttgtta aagctcttat ataaaaagc cccaaaatat tgaagttcat | 2820 |
| ctgaaatgca aggtgctttc atcaatgaac cttttcaaac ttttctatga ttgcagagaa | 2880 |
| gctttttata tacccagcat aacttggaaa caggtatctg acctattctt atttagttaa | 2940 |
| cacaagtgtg attaatttga tttctttaat tccttattga atcttatgtg atatgatttt | 3000 |
| ctggatttac agaacattag cacatgtacc ttgtgcctcc cattcaagtg aagttataat | 3060 |
| ttacactgag ggtttcaaaa ttcgactaga agtgggagata tattatttat ttatgcactg | 3120 |
| tactgtattt ttatattgct gtttaaaact tttaagctgt gcctcactta ttaaagcaca | 3180 |
| aaatgtttta cctactcctt atttacgacg caataaaata acatcaatag attttaggc | 3240 |
| tgaattaatt tgaaagcagc aatttgctgt tctcaaccat tctttcaagg cttttcattg | 3300 |
| ttcaaagtta ataaaaagt aggacaataa agtgaaaaa aaaaaaaaa aa | 3352 |

<210> SEQ ID NO 3
<211> LENGTH: 488
<212> TYPE: PRT
<213> ORGANISM: Homo sapiens

<400> SEQUENCE: 3

Met Ala Pro Ala Ala Trp Leu Arg Ser Ala Ala Arg Ala Leu Leu
1               5                   10                  15

Pro Pro Met Leu Leu Leu Leu Gln Pro Pro Leu Leu Ala Arg
            20                  25                  30

Ala Leu Pro Pro Asp Ala His His Leu His Ala Glu Arg Arg Gly Pro

```
                35                  40                  45
Gln Pro Trp His Ala Ala Leu Pro Ser Ser Pro Ala Pro Ala Pro Ala
 50                  55                  60

Thr Gln Glu Ala Pro Arg Pro Ala Ser Ser Leu Arg Pro Pro Arg Cys
 65                  70                  75                  80

Gly Val Pro Asp Pro Ser Asp Gly Leu Ser Ala Arg Asn Arg Gln Lys
                 85                  90                  95

Arg Phe Val Leu Ser Gly Gly Arg Trp Glu Lys Thr Asp Leu Thr Tyr
                100                 105                 110

Arg Ile Leu Arg Phe Pro Trp Gln Leu Val Gln Glu Gln Val Arg Gln
                115                 120                 125

Thr Met Ala Glu Ala Leu Lys Val Trp Ser Asp Val Thr Pro Leu Thr
    130                 135                 140

Phe Thr Glu Val His Glu Gly Arg Ala Asp Ile Met Ile Asp Phe Ala
145                 150                 155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
                180                 185                 190

Phe Asp Tyr Asp Glu Thr Trp Thr Ile Gly Asp Asp Gln Gly Thr Asp
            195                 200                 205

Leu Leu Gln Val Ala Ala His Glu Phe Gly His Val Leu Gly Leu Gln
    210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
            260                 265                 270

Pro Gln Ala Gly Ile Asp Thr Asn Glu Ile Ala Pro Leu Glu Pro Asp
    275                 280                 285

Ala Pro Pro Asp Ala Cys Glu Ala Ser Phe Asp Ala Val Ser Thr Ile
290                 295                 300

Arg Gly Glu Leu Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
            325                 330                 335

Gln Gly Leu Pro Ser Pro Val Asp Ala Ala Phe Glu Asp Ala Gln Gly
    340                 345                 350

His Ile Trp Phe Phe Gln Gly Ala Gln Tyr Trp Val Tyr Asp Gly Glu
            355                 360                 365

Lys Pro Val Leu Gly Pro Ala Pro Leu Thr Glu Leu Gly Leu Val Arg
    370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                405                 410                 415

Arg Val Asp Ser Pro Val Pro Arg Ala Thr Asp Trp Arg Gly Val
            420                 425                 430

Pro Ser Glu Ile Asp Ala Ala Phe Gln Asp Ala Asp Gly Tyr Ala Tyr
            435                 440                 445

Phe Leu Arg Gly Arg Leu Tyr Trp Lys Phe Asp Pro Val Lys Val Lys
450                 455                 460
```

Ala Leu Glu Gly Phe Pro Arg Leu Val Gly Pro Asp Phe Phe Gly Cys
465                 470                 475                 480

Ala Glu Pro Ala Asn Thr Phe Leu
            485

<210> SEQ ID NO 4
<211> LENGTH: 2276
<212> TYPE: DNA
<213> ORGANISM: Homo sapiens

<400> SEQUENCE: 4

```
aagcccagca gccccggggc ggatggctcc ggccgcctgg ctccgcagcg cggccgcgcg      60
cgccctcctg cccccgatgc tgctgctgct gctccagccg ccgccgctgc tggcccgggc     120
tctgccgccg gacgcccacc acctccatgc cgagaggagg gggccacagc cctggcatgc     180
agccctgccc agtagcccgg cacctgcccc tgccacgcag gaagcccccc ggcctgccag     240
cagcctcagg cctccccgct gtggcgtgcc cgacccatct gatgggctga gtgcccgcaa     300
ccgacagaag aggttcgtgc tttctggcgg gcgctgggag aagacggacc tcacctacag     360
gatccttcgg ttcccatggc agttggtgca ggagcaggtg cggcagacga tggcagaggc     420
cctaaaggta tggagcgatg tgacgccact cacctttact gaggtgcacg agggccgtgc     480
tgacatcatg atcgacttcg ccaggtactg catggggac gacctgccgt ttgatgggcc     540
tggggggcatc ctggcccatg ccttcttccc caagactcac cgagaagggg atgtccactt     600
cgactatgat gagacctgga ctatcgggga tgaccagggc acagacctgc tgcaggtggc     660
agcccatgaa tttggccacg tgctggggct gcagcacaca acagcagcca aggccctgat     720
gtccgccttc tacacctttc gctacccact gagtctcagc ccagatgact gcaggggcgt     780
tcaacaccta tatggccagc cctggcccac tgtcacctcc aggaccccag ccctgggccc     840
ccaggctggg atagacacca atgagattgc accgctggag ccagacgccc gccagatgc     900
ctgtgaggcc tcctttgacg cggtctccac catccgaggc gagctctttt tcttcaaagc     960
gggctttgtg tggcgcctcc gtgggggcca gctgcagccc ggctaccagc cattggcctc    1020
tcgccactgg cagggactgc ccagccctgt ggacgctgcc ttcgaggatg cccagggcca    1080
catttggttc ttccaaggtg ctcagtactg ggtgtacgac ggtgaaaagc cagtcctggg    1140
ccccgcaccc ctcaccgagc tgggcctggt gaggttcccg gtccatgctg ccttggtctg    1200
gggtcccgag aagaacaaga tctacttctt ccgaggcagg gactactggc gtttccaccc    1260
cagcacccgg cgtgtagaca gtcccgtgcc ccgcagggcc actgactgga gaggggtgcc    1320
ctctgagatc gacgctgcct tccaggatgc tgatggctat gcctacttcc tgcgcggccg    1380
cctctactgg aagtttgacc ctgtgaaggt gaaggctctg gaaggcttcc ccgtctcgt    1440
gggtcctgac ttctttggct gtgccgagcc tgccaacact ttcctctgac catggcttgg    1500
atgccctcag gggtgctgac ccctgccagg ccacgaatat caggctagag acccatggcc    1560
atctttgtgg ctgtgggcac caggcatggg actgagccca tgtctcctca gggggatggg    1620
gtggggtaca accaccatga caactgccgg gagggccacg caggtcgtgg tcacctgcca    1680
gcgactgtct cagactgggc agggaggctt tggcatgact aagaggaag gcagtcttg    1740
ggcccgctat gcaggtcctg gcaaacctgg ctgccctgtc tccatccctg tccctcaggg    1800
tagcaccatg gcaggactgg gggaactgga gtgtccttgc tgtatccctg ttgtgaggtt    1860
ccttccaggg gctggcactg aagcaagggt gctgggcccc catggccttc agccctggct    1920
```

| | | | | | |
|---|---|---|---|---|---|
| gagcaactgg | gctgtagggc | agggccactt | cctgaggtca | ggtcttggta | ggtgcctgca | 1980 |
| tctgtctgcc | ttctggctga | caatcctgga | aatctgttct | ccagaatcca | ggccaaaaag | 2040 |
| ttcacagtca | aatggggagg | ggtattcttc | atgcaggaga | cccaggccc | tggaggctgc | 2100 |
| aacataccto | aatcctgtcc | caggccggat | cctcctgaag | ccctttcgc | agcactgcta | 2160 |
| tcctccaaag | ccattgtaaa | tgtgtgtaca | gtgtgtataa | accttcttct | tctttttttt | 2220 |
| tttttaaact | gaggattgtc | attaaacaca | gttgttttct | aaaaaaaaaa | aaaaaa | 2276 |